US008062489B2

United States Patent
Oki et al.

(10) Patent No.: US 8,062,489 B2
(45) Date of Patent: Nov. 22, 2011

(54) METHOD FOR FORMING ARTIFICIAL LIPID MEMBRANE

(75) Inventors: Akio Oki, Kyoto (JP); Norihito Tsukahara, Kyoto (JP); Masato Suzuki, Osaka (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/971,885

(22) Filed: Dec. 17, 2010

(65) Prior Publication Data
US 2011/0083793 A1 Apr. 14, 2011

Related U.S. Application Data

(63) Continuation of application No. PCT/JP2010/002348, filed on Mar. 31, 2010.

(30) Foreign Application Priority Data

Oct. 7, 2009 (JP) .................... 2009-233292

(51) Int. Cl.
*G01N 27/327* (2006.01)
*G01N 33/92* (2006.01)
*B01L 3/00* (2006.01)

(52) U.S. Cl. ............... 204/403.01; 204/403.08; 436/71; 422/503

(58) Field of Classification Search ............ 204/403.01, 204/403.08; 205/777.5, 778; 422/99, 100; 436/71
See application file for complete search history.

(56) References Cited

U.S. PATENT DOCUMENTS
7,408,359 B2 8/2008 Ide
(Continued)

FOREIGN PATENT DOCUMENTS
JP 04-215052 8/1992
(Continued)

OTHER PUBLICATIONS

Kestin et al. The Viscosity of Aqueous KCl Solutions in the Temperature Range 25-200° C. and the Pressure Range 0.1-30 MPa, International Journal for Thermophysics, vol. 2, No. 4, 1981.*
(Continued)

*Primary Examiner* — Alex Noguerola
(74) *Attorney, Agent, or Firm* — McDermott Will & Emery LLP

(57) ABSTRACT

An object of the present invention is to provide a method for stably forming an artificial lipid membrane while suppressing the leakage and evaporation of an electrolytic solution. The present invention is an artificial lipid membrane forming method for forming an artificial lipid membrane using an artificial lipid membrane forming apparatus. The artificial lipid membrane forming apparatus comprises a first chamber, a second chamber, a dividing wall, and an artificial lipid membrane forming portion. Each of the first chamber and the second chamber has a capacity of not smaller than 10 pl and not larger than 200 μl. The artificial lipid membrane forming method of the present invention comprises the steps of: preparing the artificial lipid membrane forming apparatus; adding to the first chamber a first electrolytic solution having a viscosity of not lower than 1.3 mPa·s and not higher than 200 mPa·s; adding a lipid solution to the artificial lipid membrane forming portion; adding to the second chamber a second electrolytic solution having a viscosity of not lower than 1.3 mPa·s and not higher than 200 mPa·s; and forming the artificial lipid membrane.

14 Claims, 16 Drawing Sheets

U.S. PATENT DOCUMENTS

| | | |
|---|---|---|
| 7,828,947 B2 * | 11/2010 | Oki et al. .............. 204/403.01 |
| 2007/0035308 A1 | 2/2007 | Ide |
| 2007/0161101 A1 | 7/2007 | Takeuchi |

FOREIGN PATENT DOCUMENTS

| | | |
|---|---|---|
| JP | 05-007770 | 1/1993 |
| JP | 07-241512 | 9/1995 |
| JP | 08-152423 | 6/1996 |
| JP | 11-056389 | 3/1999 |
| JP | 2005-91308 | 4/2005 |
| JP | 2005-098718 | 4/2005 |
| JP | 2006-312141 | 11/2006 |
| JP | 2007-187560 | 7/2007 |
| JP | 2008-194573 | 8/2008 |
| JP | 2009-008618 | 1/2009 |
| WO | WO 2005/071405 A1 | 8/2005 |

OTHER PUBLICATIONS

Yasunobu Okada, "Patch Clamp Experimental Technique," Yoshioka Book Store, Sep. 25, 1996, pp. 133-139.

* cited by examiner (a)

(b)

(c)

(a)

(b)

(c)

(a)

(b)

(c)

(a)

(b)

(c)

US 8,062,489 B2

METHOD FOR FORMING ARTIFICIAL LIPID MEMBRANE

Related Applications

This application is a Continuation of PCT International Application PCT/JP2010/002348, filed on Mar. 31, 2010, which in turn claims the benefit of Japanese Application No. 2009-233292, filed on Oct. 7, 2009, the disclosures of which Applications are incorporated by reference herein.

TECHNICAL FIELD

The present invention relates to a method for forming an artificial lipid membrane used in biosensing or membrane protein analyses.

BACKGROUND ART

PTLs 1 to 3 disclose a biosensor which utilizes an excellent molecular recognition function of a receptor. Such biosensor comprises an artificial lipid membrane having receptors and ion channels.

Examples of a conventional artificial lipid membrane forming method are (1) a bubble spraying method, (2) an attaching method, and (3) μTAS (Micro Total Analysis System) (see NPL 1, for example).

FIG. 20 shows a conventional artificial lipid membrane forming method according to the bubble spraying method. In FIG. 20, the inside of a container 10 is divided by a flat plate 11 made of resin, such as Teflon (trademark) or polystyrene, having a hydrophobic property. Spaces divided by the flat plate 11 are filled with an electrolytic solution 12. A lipid solution 14 containing lipid molecules and an organic solvent is applied with a pipette 15 to a minute hole 13 formed on the flat plate 11. The surplus organic solvent contained in the lipid solution 14 applied to the minute hole 13 gradually move along a peripheral edge of the minute hole 13 to be removed. The artificial lipid membrane is formed in about 30 minutes to 3 hours after the application.

Examples of the lipid are phosphatides, such as diphytanoyl phosphatidylcholine and glycerol monooleate. Examples of the organic solvent are saturated hydrocarbons, such as decane, hexadecane, and hexane.

Each of FIGS. 21(a) to 21(c) shows a conventional artificial lipid membrane forming method according to the attaching method. In FIG. 21(a), the inside of a container 20 is divided by a flat plate 21 having a hydrophobic surface. The flat plate 21 is made of resin, such as Teflon (trademark) or polystyrene.

First, as a pretreatment, squalene is applied to a minute hole 22 formed on the flat plate 21. An electrolytic solution 23 is added through an inlet 24 to one of chambers of the container 20 such that a solution level of the electrolytic solution 23 does not exceed the height of a lower end of the minute hole 22. Next, a lipid solution (mixture of lipid molecules 25 and an organic solvent) is dropped onto the electrolytic solution 23 from above the container 20, and this mixture is left for several minutes. As shown in FIG. 21(a), a lipid monolayer is formed on a gas-liquid interface of the electrolytic solution 23. The lipid molecule 25 has a hydrophilic portion and a hydrophobic portion, and the hydrophilic portion of the lipid molecule 25 is oriented toward the electrolytic solution 23.

Then, as shown in FIG. 21(b), the electrolytic solution 23 is added through the inlet 24 until the solution level of the electrolytic solution 23 exceeds the height of an upper end of the minute hole 22.

The same steps as above are carried out in the other chamber of the container 20. To be specific, as shown in FIG. 21(c), an electrolytic solution 26 is added through an inlet 27 such that the solution level of the electrolytic solution 26 does not exceed the height of the lower end of the minute hole 22. Next, the lipid solution is dropped onto the electrolytic solution 26 from above the container 20, and this mixture is left for several minutes. The lipid monolayer is formed on the gas-liquid interface of the electrolytic solution 26. The electrolytic solution 26 is added through the inlet 27 until the solution level of the electrolytic solution 26 exceeds the height of the upper end of the minute hole 22. Thus, this lipid monolayer formed later is attached to the lipid monolayer formed in advance at the minute hole 22. As a result, the artificial lipid membrane is formed at the minute hole 22.

It requires a high degree of skill to form the artificial lipid membrane stably and highly reproducibly by each of the above-described two methods.

In order to form further simple artificial lipid membranes, each of PTLs 1 to 4 discloses a method for forming the artificial lipid membrane using the μTAS technique.

FIG. 22 shows a compact artificial lipid membrane forming apparatus which is described in PTL 1 and uses the μTAS technique. The artificial lipid membrane forming apparatus shown in FIG. 22 comprises a first chamber 31 and a second chamber 33 which is isolated from the first chamber 31 by a dividing wall 32. The dividing wall 32 comprises at least one small hole 34 through which the first chamber 31 and the second chamber 33 are fluidically communicated with each other. The artificial lipid membrane is formed as below using the artificial lipid membrane forming apparatus. First, the first chamber 31 is filled with a first aqueous solution, and the second chamber 33 is then filled with a lipid solution. The first aqueous solution is brought in contact with the lipid solution through the small hole 34. Further, the lipid solution with which the second chamber 33 is filled is replaced with a second aqueous solution. Thus, an artificial lipid membrane 35 is formed at the small hole 34.

Citation List

Patent Literature
    PTL 1: Japanese Laid-Open Patent Application Publication No. 2005-098718 (page 15, FIG. 5)
    PTL 2: Japanese Laid-Open Patent Application Publication No. Hei5-007770 (page 3, FIG. 1)
    PTL 3: Japanese Laid-Open Patent Application Publication No. Hei8-152423 (page 3, FIG. 1)
    PTL 4: Japanese Laid-Open Patent Application Publication No. Hei4-215052 (page 5, FIG. 1)
Non Patent Literature
    NPL 1: "Patch Clamp Experimental Technique" written by Yasunobu Okada, published on Sep. 25, 1996 by Yoshioka Book Store (pages 133-139)

SUMMARY OF INVENTION

Technical Problem

Since the artificial lipid membrane forming apparatus disclosed in PTL 1 is compact and easy to carry, the convenience thereof is extremely excellent. However, in a case where the artificial lipid membrane forming apparatus receives vibrations, is inclined, or is turned over while the apparatus is being carried during or after the formation of the artificial lipid membrane, the electrolytic solution in the artificial lipid membrane forming apparatus may leak through an opening of the inlet or outlet to the outside of the chamber. As a result, the periphery of the artificial lipid membrane forming apparatus is contaminated by the electrolytic solution. Further, since the compact artificial lipid membrane forming apparatus holds a minute amount of electrolytic solution, the electrolytic solution rapidly evaporates, and the artificial lipid membrane cannot be stably formed.

An object of the present invention is to provide a method for stably forming an artificial lipid membrane by solving the above conventional problems and preventing an electrolytic solution from leaking to the outside of a chamber and the electrolytic solution from rapidly evaporating.

Solution to Problem

The present invention relates to a method for forming an artificial lipid membrane, comprising the steps of: (A) preparing an artificial lipid membrane forming apparatus (100) comprising a first chamber (104), a second chamber (105), a dividing wall (102) sandwiched between the first chamber (104) and the second chamber (105), and an artificial lipid membrane forming portion (103) that consists of a through hole formed on the dividing wall (102), the first chamber (104) having a capacity of not smaller than 10 pl and not larger than 200 μl, the second chamber (105) having a capacity of not smaller than 10 pl and not larger than 200 μl; (B) adding to the first chamber (104) a first electrolytic solution (201) having a viscosity of not lower than 1.3 mPa·s and not higher than 200 mPa·s; (C) adding to the artificial lipid membrane forming portion (103) a lipid solution (202) containing a lipid (203) and an organic solvent; (D) adding to the second chamber (105) a second electrolytic solution (204) having a viscosity of not lower than 1.3 mPa·s and not higher than 200 mPa·s to sandwich the lipid solution (202) between the first electrolytic solution (201) and the second electrolytic solution (204); and (E) removing the organic solvent to form an artificial lipid membrane at the artificial lipid membrane forming portion (103).

It is preferable that at least one of the first electrolytic solution (201) and the second electrolytic solution (204) contain an organic compound having a hydroxyl group.

It is preferable that the organic compound having the hydroxyl group be an alcohol.

It is preferable that the alcohol be a lower alcohol.

It is also preferable that the alcohol be glycerin.

It is preferable that at least one of the first electrolytic solution (201) and the second electrolytic solution (204) contain a polymer.

It is preferable that the polymer be a polyvinyl alcohol.

It is preferable that in Step (B), the first electrolytic solution (201) be added to the first chamber (104) by an ink-jet method.

It is preferable that in Step (D), the second electrolytic solution (204) be added to the second chamber (105) by an ink-jet method.

It is preferable that in Step (C), the lipid solution (202) be added to the artificial lipid membrane forming portion (103) by an ink-jet method.

It is preferable that the present invention further comprises the step of: (F) after Step (E), implanting at least one of a receptor and an ion channel in the artificial lipid membrane.

It is preferable that in Step (B), the first chamber (104) be filled with the first electrolytic solution (201).

It is preferable that in Step (D), the second chamber (105) be filled with the second electrolytic solution (204).

The above object, other objects, features and advantages of the present invention will be made clear by the following detailed explanation of preferred embodiments with reference to the attached drawings.

Advantageous Effects of Invention

In accordance with the artificial lipid membrane forming method of the present invention, the leakage of the electrolytic solution from the chamber can be prevented by increasing the viscosity of the electrolytic solution while maintaining the flowability. As a result, the contamination around the apparatus by the electrolytic solution can be prevented. Further, since the electrolytic solution can be prevented from rapidly evaporating, the artificial lipid membrane can be stably formed.

DESCRIPTION OF EMBODIMENTS

Embodiment 1

Hereinafter, Embodiment 1 of the present invention will be explained in reference to the drawings.

Step A: Preparing Step

Figure 1:
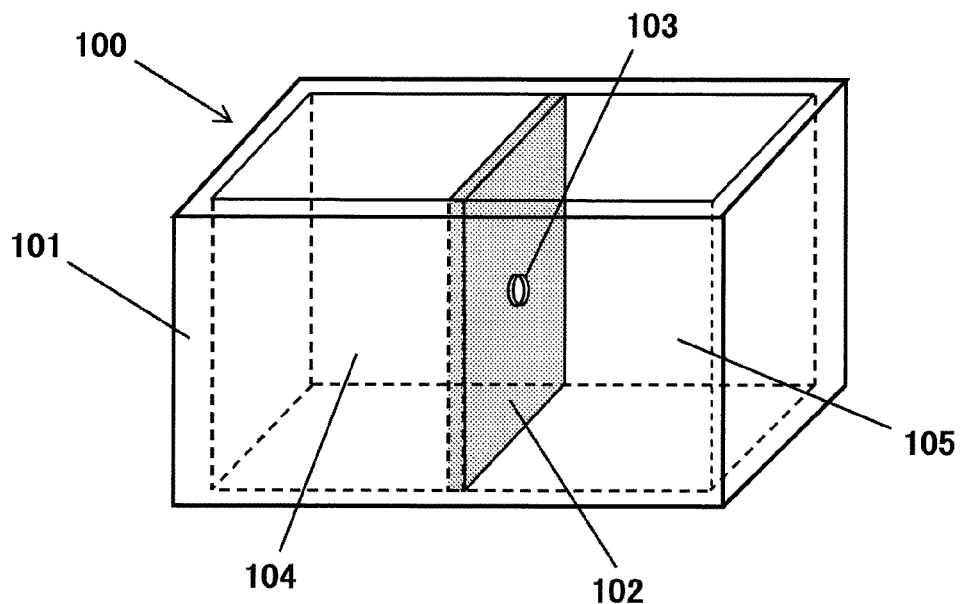
FIG. 1 shows an oblique projection view of an artificial lipid membrane forming apparatus of Embodiment 1.
Figure 2:
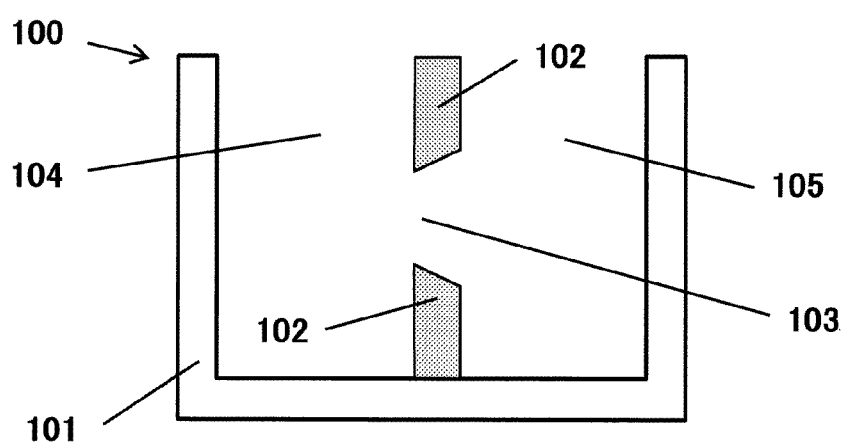
FIG. 2 shows a cross-sectional view of the artificial lipid membrane forming apparatus of Embodiment 1.

FIGS. 1 and 2 respectively show an oblique projection view and cross-sectional view of an artificial lipid membrane forming apparatus 100 in Embodiment 1 of the present invention.

In Embodiment 1, the artificial lipid membrane forming apparatus 100 comprises a container 101. Examples of a material of the container 101 are organic materials and inorganic materials. The organic materials are preferable.

The organic material may be a thermoplastic resin or a thermosetting resin. The organic material may be a commodity plastic, an engineering plastic, or a super engineering plastic. Examples of the organic material are phenol resins, melamine resins, epoxy resins, polyester resins, polyurethane resins, polyimide resins, polyethylene, polycarbonate, polyvinyl acetate, ABS (acrylonitrile butadiene styrene) resins, acryl, polyethylene terephthalate, vinyl chloride, polypropylene, polystyrene, polysulfone, PEEK (trademark), polyacetal, cyclic polyolefin, polyphenylene sulfide, polytetrafluoroethylene, and polyamidimide. The organic material may be a composite resin.

As the inorganic material, glass is preferable. Soda glass, quartz, borosilicate glass, low melting point glass, or photosensitive glass may be used. As the inorganic material other than glass, silicon, germanium, indium phosphide, gallium arsenide, gallium nitride, aluminum oxide, silicon oxide, or silicon nitride may be used.

The material of the container 101 may be a combination of a plurality of organic materials or a combination of a plurality of inorganic materials. It is preferable that the material of the container 101 have an insulation property regardless of the organic material or the inorganic material.

It is preferable that at least a part of an outer peripheral surface of the container 101 has a hydrophilic property. In order to give the hydrophilic property to at least the part of the outer peripheral surface of the container 101, at least the part of the outer peripheral surface of the container 101 may be subjected to an oxygen plasma treatment or may be covered with a hydrophilic material. It is preferable that the material of the container 101 be transparent such that the artificial lipid membrane can be observed. However, the material of the container 101 may be opaque.

It is preferable that a capacity of the container 101 be not smaller than 2 pl and not larger than 2 ml in light of operability. It is more preferable that the capacity of the container 101 be not smaller than 1 nl and not larger than 400 µl. It is preferable that the container 101 be a rectangular solid. However, the container 101 may be a cylindrical shape or a polygon. The container 101 may be a passage or a chamber.

It is preferable that the container 101 be molded by machine work. It is preferable that the machine work be injection molding, extrusion molding, compression molding, hollow molding, cutting operation, molding, sand blasting, dry etching, wet etching, nanoimprint, milling, photocuring, lithography, or hot embossing. It is also preferable that the container 101 be processed by a semiconductor process.

A dividing wall 102 is provided inside the container 101. It is preferable that the dividing wall 102 be provided to divide the container 101 into at least two chambers. It is preferable that the dividing wall 102 be provided at a center portion of the container 101. However, the dividing wall 102 may be provided at an end portion of the container 101.

Any of the materials, each of which can be used as the material of the container 101, may be used as the material of the dividing wall 102.

A part of the surface of the dividing wall 102 may be covered with a thin film made of a material different from the material of the dividing wall 102. It is preferable that the thickness of the thin film covering the surface of the dividing wall 102 be not smaller than 10 nm and not larger than 100 µm. A part of the surface of the dividing wall 102 may be covered with a self-assembled film (SAM film) or a thin film made of a water repellent material.

It is preferable that the material of the dividing wall 102 have the insulation property regardless of the organic material or the inorganic material. It is preferable that an electrical resistivity of the material of the dividing wall 102 be not less than $10^{10}$ Ω cm, and it is more preferable that the electrical resistivity of the material of the dividing wall 102 be not less than $10^{12}$ Ω cm. It is preferable that a relative permittivity of the material of the dividing wall 102 be not less than 2.0 and not more than 50.0, and it is more preferable that the relative permittivity of the material of the dividing wall 102 be not less than 2.0 and not more than 15.0.

It is preferable that the surface of the dividing wall 102 be water-repellent. It is preferable that a contact angle of the surface of the dividing wall 102 be not smaller than 90°, and it is more preferable that the contact angle of the surface of the dividing wall 102 be not smaller than 120° and not larger than 150°.

It is most preferable that the dividing wall 102 have a plate shape. However, the dividing wall 102 may have a film shape. It is preferable that the thickness of the dividing wall 102 be not smaller than 10 nm and not larger than 1 mm, and it is more preferable that the thickness of the dividing wall 102 be not smaller than 30 µm and not larger than 500 µm. The thickness of the dividing wall 102 may be or may not be uniform over the entire surface thereof. It is preferable that the area of the dividing wall 102 be not smaller than 1 µm$^2$ and not larger than 100 cm$^2$, and it is more preferable that the area of the dividing wall 102 be not smaller than 100 µm$^2$ and not larger than 1 cm$^2$.

It is preferable that the dividing wall 102 be molded by machine work. It is preferable that the machine work be injection molding, extrusion molding, compression molding, hollow molding, cutting operation, solution casting, stretching, molding, sand blasting, dry etching, wet etching, nanoimprint, milling, photocuring, lithography, or hot embossing. It is also preferable that the dividing wall 102 be processed by a semiconductor process.

One dividing wall 102 may be provided inside the container 101, or two or more dividing walls 102 may be provided inside the container 101.

Figure 3:
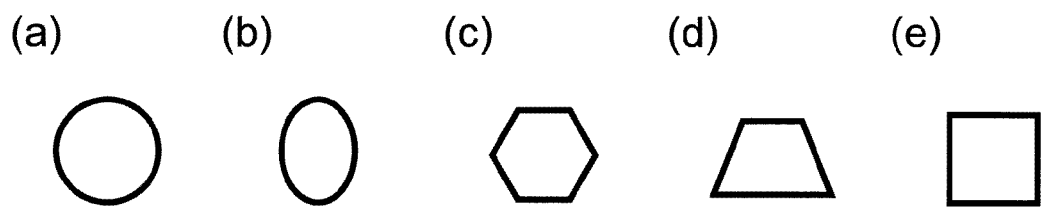
FIG. 3 shows a cross section of a through hole that is one example of an artificial lipid membrane forming portion of Embodiment 1.

It is preferable that an artificial lipid membrane forming portion 103 be provided at a center portion of the dividing wall 102. The artificial lipid membrane forming portion 103 may be provided at an end portion of the dividing wall 102. It is most preferable that the artificial lipid membrane forming portion 103 be a through hole formed on the dividing wall 102. It is preferable that the cross section of the through hole be circular. FIGS. 3 show the cross section of the through hole as the artificial lipid membrane forming portion 103 and show the cross section when viewed from a normal direction of the dividing wall 102. FIG. 3(a) shows that the cross section of the through hole as the artificial lipid membrane forming portion 103 is circular. It is preferable that the cross section of the through hole be circular since a force applied to the artificial lipid membrane is uniformly distributed. As shown in FIGS. 3(b) to 3(e), the cross section of the through hole may be oval, polygonal, trapezoidal, or quadrangular. It is more preferable that the through hole have a tapered shape as shown in FIG. 2.

In a case where the artificial lipid membrane forming portion 103 is a through hole having a circular cross section, it is preferable that the diameter of the artificial lipid membrane forming portion 103 be not smaller than 10 nm and not larger than 1 mm, and it is more preferable that the diameter of the artificial lipid membrane forming portion 103 be not smaller than 50 nm and not larger than 200 μm. It is preferable that the area of the artificial lipid membrane forming portion 103, that is, the area of each of the shapes shown in FIGS. 3(a) to 3(e) be not smaller than 75 nm$^2$ and not larger than 0.75 mm$^2$. It is preferable that an inner wall of the artificial lipid membrane forming portion 103 be smooth. However, in order to stabilize the artificial lipid membrane, the inner wall of the artificial lipid membrane forming portion 103 may have a concave-convex structure or a groove structure.

The artificial lipid membrane forming portion 103 may be molded in the same manner as the dividing wall 102.

One artificial lipid membrane forming portion 103 may be formed on the dividing wall 102, or a plurality of artificial lipid membrane forming portions 103 may be formed on the dividing wall 102. It is preferable that the plurality of artificial lipid membrane forming portions 103 be two-dimensionally arranged in an array. It is preferable that the plurality of artificial lipid membrane forming portions 103 be arranged in a square lattice pattern, a rhombic lattice pattern, a hexagonal lattice pattern, a simple rectangular lattice pattern, or a face-centered rectangular lattice pattern. The plurality of artificial lipid membrane forming portions 103 may be the same in shape as one another or may be different in shape from one another. The plurality of artificial lipid membrane forming portions 103 may be the same in area as one another or may be different in area from one another.

A first chamber 104 is provided at one end of the container 101. It is preferable that the first chamber 104 be provided between an inner wall of the container 101 and the dividing wall 102, and it is most preferable that the first chamber 104 be formed by the inner wall of the container 101 and the dividing wall 102. In light of the operability, it is preferable that the capacity of the first chamber 104 be not smaller than 1 pl and not larger than 1 ml, and it is more preferable that the capacity of the first chamber 104 be not smaller than 10 pl and not larger than 200 μl. It is preferable that the first chamber 104 have an inlet through which the electrolytic solution is added. It is preferable that the first chamber 104 have an outlet through which the electrolytic solution is discharged. The first chamber 104 may be connected to an electrolytic solution reservoir through a passage. The capacity of the electrolytic solution reservoir may be or may not be included in the capacity of the first chamber 104. A cover or a stopple may be provided on an opening of the first chamber 104, or a film may be attached to the opening of the first chamber 104.

A second chamber 105 is provided on an opposite side of the first chamber 104 via the dividing wall 102. It is preferable that the second chamber 105 be provided between the inner wall of the container 101 and the dividing wall 102, and it is most preferable that the second chamber 105 be formed by the inner wall of the container 101 and the dividing wall 102. In light of the operability, it is preferable that the capacity of the second chamber 105 be not smaller than 1 pl and not larger than 1 ml, and it is more preferable that the capacity of the second chamber 105 be not smaller than 10 pl and not larger than 200 μl. The volume of the second chamber 105 may be the same as or different from the volume of the first chamber 104. It is preferable that the second chamber 105 have an inlet through which the electrolytic solution is added. It is preferable that the second chamber 105 have an outlet through which the electrolytic solution is discharged. The second chamber 105 may be connected to the electrolytic solution reservoir via a passage. The capacity of the electrolytic solution reservoir may be or may not be included in the capacity of the second chamber 105. A cover or a stopple may be provided on an opening of the second chamber 105, or a film may be attached to the opening of the second chamber 105.

Figure 4:
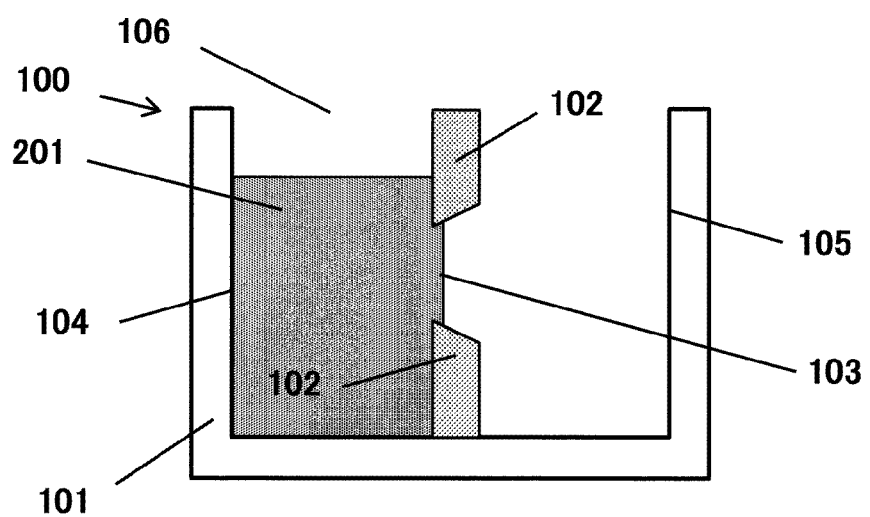
FIG. 4 shows a first electrolytic solution adding step of Embodiment 1.
Figure 5:
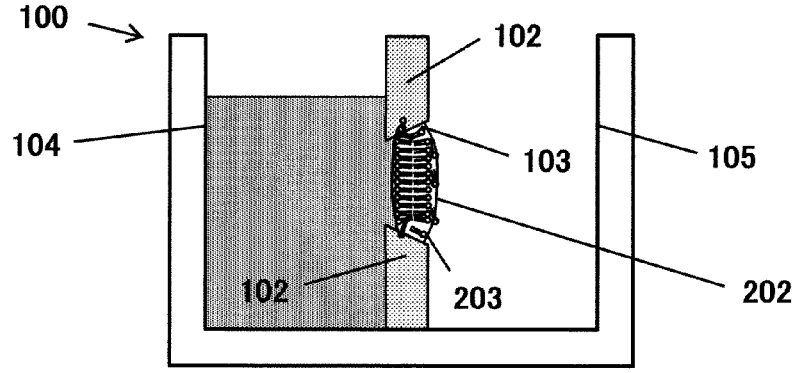
FIG. 5 shows steps from a lipid adding step to an artificial lipid membrane forming step in Embodiment 1.
Figure 5:
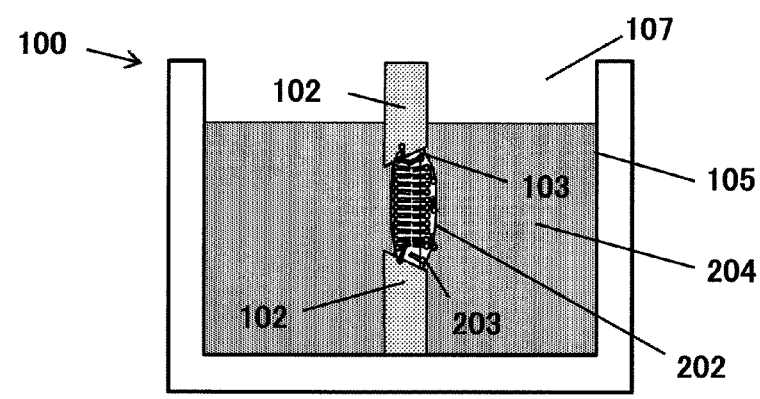
Figure 5:
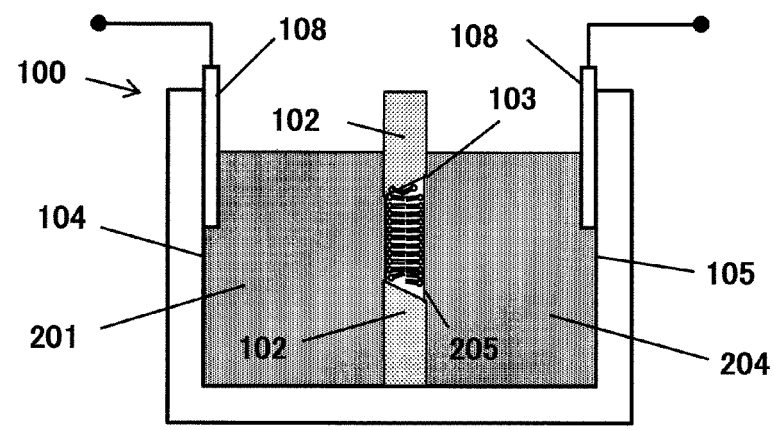

Next, a procedure of forming the artificial lipid membrane will be explained. Each of FIGS. 4 and 5 shows an artificial lipid membrane forming method in Embodiment 1 of the present invention. In FIGS. 4 and 5, the same reference signs are used for the same components as in FIGS. 1 and 2, and explanations thereof are omitted.

Step B: First Electrolytic Solution Adding Step

FIG. 4 shows a first electrolytic solution adding step. In the first electrolytic solution adding step, a first electrolytic solution 201 is added through a first opening 106 to the first chamber 104, and the first chamber 104 is filled with the first electrolytic solution 201. It is preferable that the first electrolytic solution 201 do not flow through the artificial lipid membrane forming portion 103 to move from the first chamber 104 to the second chamber 105.

It is preferable that the first electrolytic solution 201 contain KCl, and it is more preferable that the first electrolytic solution 201 be an isotonic KCl solution. It is preferable that the first electrolytic solution 201 be the same as a physiological condition in a cell. It is preferable that pH of the first electrolytic solution 201 be about seven. The first electrolytic solution 201 may be a buffer solution, such as HEPES, a phosphate buffer solution (PBS), or a phosphate buffer physiological saline solution or may be a common solution used in electrophysiological experiments. It is preferable that a $Ca^{2+}$ concentration of the first electrolytic solution 201 be 10 to 100 nM. In order to adjust the $Ca^{2+}$ concentration, $Ca^{2+}$ chelators, such as EGTA, may be used.

It is preferable that the first electrolytic solution 201 contain a Tyrode solution. It is preferable that the first electrolytic solution 201 contain 137 mM of NaCl, 2.68 mM of KCl, 1.8 mM of $CaCl_2$, 0.32 mM of $NaH_2PO_4$, 5.56 mM of Glucose, and 1.16 mM of $NaHCO_3$. The first electrolytic solution 201 may contain 140 mM of NaCl, 5.4 mM of KCl, 1.8 mM of $CaCl_2$, 1 mM of $MgCl_2$, 0.3 mM of $NaHPO_4$, 5 mM of Glucose, and 5 mM of HEPES (pH7.4). The first electrolytic solution 201 may contain 140 mM of KCl, 1 mM of $MgCl_2$, 1 mM of $CaCl_2$, 10 mM of EGTA, 2 mM of Mg-ATP, and 10 mM of NaOH-HEPES (pH7.3).

It is preferable that $Cl^-$ in the first electrolytic solution 201 be replaced with membrane-impermeant negative ions, such as $SO_4^{2-}$, Methanesulfonate, gluconate, glutamate, or aspartate. It is preferable that the first electrolytic solution 201 be refrigerated at −20° C. to prevent microorganisms from multiplying. It is preferable that positive ions in the first electrolytic solution 201 be replaced with membrane-impermeant organic bases. It is preferable that the positive ions in the first electrolytic solution 201 be replaced with tetraechylammonium or N-methyl-D-glucamine. It is preferable that EGTA contained in the first electrolytic solution 201 be replaced with BAPTA. The first electrolytic solution 201 may contain ATP. In order to maintain the function of the receptor, the first electrolytic solution 201 may contain 0.1 to 0.3 mM of GTP.

It is preferable that the viscosity of the first electrolytic solution 201 be not lower than 1.3 mPa·s and not higher than 200 mPa·s. It is preferable that the first electrolytic solution 201 have flowability in order to reduce voltage drop and increase ion conductance. It is preferable that the first electrolytic solution 201 be a liquid form or a semiliquid form.

It is preferable that the viscosity of the first electrolytic solution 201 be adjusted with a water-soluble material. It is preferable that the viscosity of the first electrolytic solution 201 be adjusted with a thickener. The viscosity of the first electrolytic solution 201 may be adjusted with an organic compound having a hydrophilic functional group, such as a hydroxyl group, a carboxyl group, an amino group, or a sulfonic group. As the organic compound, an organic compound having 1 to 10 carbons is preferable, and an organic compound having 1 to 5 carbons is more preferable.

It is preferable that the viscosity of the first electrolytic solution 201 be adjusted with alcohol. The alcohol may be monovalent alcohol or polyhydric alcohol. It is preferable that the alcohol be a lower alcohol, such as glycerin.

The viscosity of the first electrolytic solution 201 may be adjusted with sugar or sugar alcohol, such as isopropyl alcohol, ethylene glycol, sorbitol, xylitol, dipropylene glycol, butylene glycol, polyethylene glycol, polyoxyethylene methyl glucoside, maltitol, mannitol, or glucose. As the sugar, monosaccharide, disaccharide, trisaccharide, tetrasaccharide, or polysaccharide may be used.

It is preferable that the viscosity of the first electrolytic solution 201 be higher than the viscosity (1.0 mPa·s) of pure water having a temperature of 20° C.

The viscosity of the first electrolytic solution 201 may be adjusted with a polymer. The viscosity of the first electrolytic solution 201 may be adjusted with the polymer having a hydrophilic functional group, such as a hydroxyl group, a carboxyl group, an amino group, or a sulfonic group. Polyvinyl alcohol is preferable as the polymer, but polyacrylamide or 2-hydroxyethyl methacrylate (HEMA) may also be used. The polymer may be a homopolymer or a copolymer.

It is preferable that the polymer be a synthetic polymer. However, the polymer may be a semi-synthetic polymer or a natural polymer. As the polymer, gum arabic, carboxy vinyl polymer, alginate sodium, propylene glycol alginate, ethyl cellulose, carboxymethylcellulose sodium, xanthane gum, synthetic sodium silicate, synthetic magnesium silicate, dimethyl distearyl ammonium hectorite, cyclodextrin, sodium polyacrylate, gelatin, casein, collagen, hyaluronic acid, albumin, pectin, tamarind gum, guar gum, carrageenan or carob bean gum may be used.

It is preferable that a material for adjusting the viscosity of the first electrolytic solution 201 be a material which stabilizes a membrane protein, such as the artificial lipid membrane.

In light of the ease of the addition, it is preferable that the concentration of the material for adjusting the viscosity of the first electrolytic solution 201 be not lower than 1% and not higher than 99%, and it is more preferable that the concentration of the material for adjusting the viscosity of the first electrolytic solution 201 be not lower than 1% and not higher than 50%. In light of the ease of the addition, it is preferable that the concentration of the material for adjusting the viscosity of the first electrolytic solution 201 be not lower than 0.087 w/w % and not higher than 20 w/w %, and it is more preferable that the concentration of the material for adjusting the viscosity of the first electrolytic solution 201 be not lower than 0.087 w/w % and not higher than 12 w/w %. It is preferable that a glycerin concentration of the first electrolytic solution 201 be not lower than 1% and not higher than 99%, and it is more preferable that the glycerin concentration of the first electrolytic solution 201 be not lower than 1% and not higher than 50%. It is preferable that a PVA concentration of the first electrolytic solution 201 be not lower than 0.087 w/w % and not higher than 12 w/w %. In the present specification, "%" is used to show a volume concentration, and "w/w %" is used to show a weight concentration.

In order to reduce the voltage drop, it is preferable that the electrical resistivity of the first electrolytic solution 201 be not lower than 1 µΩm and not higher than 100 kΩm, and it is more preferable that the electrical resistivity of the first electrolytic solution 201 be not lower than 1 mΩm and not higher than 10 Ωm. It is preferable that the first electrolytic solution 201 be transparent such that the artificial lipid membrane can be observed. However, the first electrolytic solution 201 may be opaque.

It is preferable that the amount of the first electrolytic solution 201 added to the first chamber 104 be not smaller than 10 pl and not larger than 200 µl, and it is more preferable that the amount of the first electrolytic solution 201 added to the first chamber 104 be not smaller than 1 nl and not larger than 200 µl. It is most preferable that the first electrolytic solution 201 remain still. However, the first electrolytic solution 201 may be flowing. It is preferable that in a case where the first electrolytic solution 201 is flowing, the amount of the first electrolytic solution 201 which practically involves the formation of the artificial lipid membrane be within the above range. After the first electrolytic solution 201 is added to the first chamber 104, the surplus first electrolytic solution 201 may be discharged to adjust the amount of the first electrolytic solution 201 in the first chamber 104.

It is preferable that the first electrolytic solution 201 be added to the first chamber 104 by using a pipette. However, the first electrolytic solution 201 may be added to the first chamber 104 by using a tube, a passage, a dropper, or a syringe. The first electrolytic solution 201 may be added to the first chamber 104 continuously or intermittently. The first electrolytic solution 201 may be added to the first chamber 104 as liquid droplets. As a method for adding the liquid droplets of the first electrolytic solution 201, an ink-jet method, an electrostatic spraying method, an ultrasound method, a dot impact method, or a minute liquid droplet applying method may be used.

The ink-jet method is a method for converting a liquid into minute liquid droplets and adding the droplets to a target position. The minute liquid droplet applying method is a method for filling a capillary having a thinly narrowed tip end with a liquid and causing a needle inserted in a capillary tube to move to add the liquid filled in the capillary. It is most preferable that the ink-jet method be a piezo type. However, the ink-jet method may be a thermal type. The minute liquid droplet applying method is a method for providing a needle in a capillary having an opening at its tip end and applying the liquid filled in the capillary to a target by the moving the needle.

The first electrolytic solution 201 is added to the first chamber 104 manually, semi-manually, or automatically. It is preferable that an adding time of the first electrolytic solution 201 be not shorter than 1 microsecond and not longer than 10 seconds, and it is more preferable that the adding time of the first electrolytic solution 201 be not shorter than 1 microsecond and not longer than 1 second. An adding speed of the first electrolytic solution 201 may be constant or may change in the first electrolytic solution adding step.

In order to suppress drying of the first electrolytic solution 201, it is preferable that the first electrolytic solution 201 be maintained at room temperature in the first electrolytic solution adding step. It is preferable that the first electrolytic solution 201 be maintained at a temperature of not lower than 0° C. and not higher than 40° C., and it is more preferable that the first electrolytic solution 201 be maintained at a temperature of not lower than 10° C. and not higher than 30° C. It is preferable that a relative humidity around the artificial lipid membrane forming apparatus 100 be maintained to be not lower than 50% and not higher than 100% in the first electrolytic solution adding step.

It is preferable that dusts and impurities contained in the first electrolytic solution 201 be removed with a membrane filter.

It is preferable that the first electrolytic solution 201 be added to the first chamber 104 by capillary force, gravity, surface tension, or centrifugal force in the first electrolytic solution adding step.

In the first electrolytic solution adding step, the termination of the addition of the first electrolytic solution 201 to the first chamber 104 may be detected. The termination of the addition may be detected by observation using an optical microscope or may be detected by providing a plurality of electrodes at the first chamber 104 and measuring an electric conductivity. It is preferable that the first electrolytic solution 201 be added to the first chamber 104 in the first electrolytic solution adding step until the first electrolytic solution 201 exceeds an upper end of the artificial lipid membrane forming portion 103.

It is most preferable that the first electrolytic solution 201 be a uniform electrolytic solution having a single viscosity. The first electrolytic solution 201 may be an electrolytic solution that is a combination of a plurality of electrolytic solutions, each having the viscosity of not lower than 1.3 mPa·s and not higher than 200 mPa·s. The viscosity of the first electrolytic solution 201 may have gradient. The gradient of the viscosity of the first electrolytic solution 201 may be continuous or discontinuous.

The first electrolytic solution 201 is minute in amount. Therefore, if the viscosity of the first electrolytic solution 201 is too low, the first electrolytic solution 201 evaporates in some cases while providing a cover or a stopple on the opening of the first chamber 104 or the second chamber 105 or attaching a film to the opening. On this account, the operations require extra attention.

Step C: Lipid Solution Adding Step

FIG. 5(a) shows a lipid solution adding step. In the lipid solution adding step, a lipid solution 202 is added to the artificial lipid membrane forming portion 103. It is preferable that the lipid solution 202 be added from the second chamber 105 side in the lipid solution adding step.

It is preferable that the lipid solution 202 be a solution prepared by dispersing lipids 203 in an organic solvent. It is preferable that the lipid 203 be a complex lipid containing phosphoric acid or sugar in molecules. The lipids 203 may contain simple lipids or derived lipids. It is most preferable that the lipid 203 be phosphatide. However, glycolipids, lipolipids, sulfolipids, sphingophospholipids, glycerophospholipids, azolectin, or the other naturally-derived lipids may be used as the lipids 203, or synthetic lipids may be used as the lipids 203. The synthetic lipid is more preferable than the naturally-derived lipid since a highly pure and chemically stable reagent is easily obtained. As the lipid 203, diphytanoyl phosphatidylcholine, glycerol monooleate, phosphatidylcholine, phosphatidyl ethanolamine, phosphatidylserine, or dipalmitoyl phosphatidylcholine may be used. It is preferable that a fatty acid portion of the lipid 203 be a saturated fatty acid or unsaturated fatty acid having 10 to 20 carbons. As the lipid 203, one type of lipid may be used, or a lipid prepared by mixing two or more types of lipids may be used.

It is preferable that the organic solvent contained in the lipid solution 202 be saturated hydrocarbon, such as decane, hexadecane, hexane, or chloroform. It is preferable that the concentration of the lipid 203 with respect to the organic solvent be 1 to 50 mg/ml, and it is more preferable that the concentration of the lipid 203 with respect to the organic solvent be 4 to 40 mg/ml.

In addition to the lipids 203 and the organic solvent, the lipid solution 202 may contain phosphatidylserine or phosphatidyl inositol in order to give net surface electric charge to the artificial lipid membrane. It is preferable that the surface electric charge of the artificial lipid membrane be negative. Phosphatidylserine or phosphatidyl inositol may be mixed with the lipid solution 202 before the lipid solution adding step or after an artificial lipid membrane forming step.

It is preferable that in addition to the lipids 203 and the organic solvent, the lipid solution 202 contain a biological membrane protein or secretory protein, such as a receptor, an ion channel, or a G protein. The lipid solution 202 may contain polypeptide, such as gramicidin. The lipid solution 202 may contain one type of biological membrane protein, secretory protein, or polypeptide or may contain plural types of biological membrane proteins, secretory proteins, or polypeptides. The biological membrane protein, the secretory protein, or the polypeptide may be introduced to the artificial lipid membrane by being mixed with the lipid solution 202 before the lipid solution adding step or may be introduced to the artificial lipid membrane after the artificial lipid membrane forming step.

In a case where the biological membrane protein, the secretory protein, or the polypeptide is introduced to the artificial lipid membrane after the artificial lipid membrane forming step, the biological membrane protein, the secretory protein, or the polypeptide may be once incorporated in a vesicle and the vesicle may be fused with the artificial lipid membrane, or a known mixing technique may be used. In a case where the biological membrane protein, the secretory protein, or the polypeptide is introduced to the artificial lipid membrane after the artificial lipid membrane forming step, a mechanism configured to mix these may be provided in the artificial lipid membrane forming apparatus 100.

In light of the ease of the formation of the artificial lipid membrane, it is preferable that the amount of the lipid solution 202 added to the artificial lipid membrane forming portion 103 be not smaller than 1 pl and not larger than 10 μl, and it is more preferable that the amount of the lipid solution 202 added to the artificial lipid membrane forming portion 103 be not smaller than 1 nl and not larger than 2μl.

It is preferable that the lipid solution 202 be added by a pipette. However, the lipid solution 202 may be added by a tube, a flow channel, a dropper, or a syringe. The lipid solution 202 may be added continuously or intermittently. The lipid solution 202 may be added as liquid droplets. The lipid solution 202 may be added to the artificial lipid membrane forming portion 103 by the ink-jet method, the minute liquid droplet applying method, the dot impact method, the electrostatic spraying method, or the ultrasound method. It is most preferable that the ink-jet method be the piezo type. However, the ink-jet method may be the thermal type.

The lipid solution 202 is added to the artificial lipid membrane forming portion 103 manually, semi-manually, or automatically. It is preferable that the adding time of the lipid solution 202 be not shorter than 1 microsecond and not longer than 10 seconds, and it is more preferable that the adding time of the lipid solution 202 be not shorter than 1 microsecond and not longer than 1 second. The adding speed of the lipid solution 202 may be constant or may change in the lipid solution adding step.

It is preferable that the lipid solution 202 be added to the artificial lipid membrane forming portion 103 by the capillary force, the gravity, the surface tension, or the centrifugal force in the lipid solution adding step.

In the lipid solution adding step, the termination of the addition of the lipid solution 202 to the artificial lipid membrane forming portion 103 may be detected. The termination of the addition may be detected by observation using an optical microscope or may be detected by providing a plurality of electrodes at the dividing wall 102 and measuring an electric conductivity.

The first electrolytic solution 201 is minute in amount. Therefore, if the viscosity of the first electrolytic solution 201 is too low, the first electrolytic solution 201 evaporates in some cases while adding the lipid solution to the artificial lipid membrane forming portion 103 by using a pipette. On this account, the operations require extra attention.

Step D: Second Electrolytic Solution Adding Step

FIG. 5(b) shows a second electrolytic solution adding step. In the second electrolytic solution adding step, a second electrolytic solution 204 is added through a second opening 107 to the second chamber 105.

It is preferable that the second electrolytic solution 204 contain KCl, and it is more preferable that the second electrolytic solution 204 be an isotonic KCl solution. It is preferable that the second electrolytic solution 204 be the same as a physiological condition in a cell. It is preferable that pH of the second electrolytic solution 204 be about seven. The second electrolytic solution 204 may be a buffer solution, such as HEPES, a phosphate buffer solution (PBS), or a phosphate buffer physiological saline solution or may be a common solution used in electrophysiological experiments. It is preferable that the $Ca^{2+}$ concentration of the second electrolytic solution 204 be 10 to 100 nM. In order to adjust the $Ca^{2+}$ concentration, $Ca^{2+}$ chelators, such as EGTA, may be used.

It is preferable that the second electrolytic solution 204 contain a Tyrode solution. It is preferable that the second electrolytic solution 204 contain 137 mM of NaCl, 2.68 mM of KCl, 1.8 mM of $CaCl_2$, 0.32 mM of $NaH_2PO_4$, 5.56 mM of Glucose, and 1.16 mM of $NaHCO_3$. The second electrolytic solution 204 may contain 140 mM of NaCl, 5.4 mM of KCl, 1.8 mM of $CaCl_2$, 1 mM of $MgCl_2$, 0.3 mM of $NaHPO_4$, 5 mM of Glucose, and 5 mM of HEPES (pH7.4). The second electrolytic solution 204 may contain 140 mM of KCl, 1 mM of $MgCl_2$, 1 mM of $CaCl_2$, 10 mM of EGTA, 2 mM of Mg-ATP, and 10 mM of NaOH-HEPES (pH7.3).

It is preferable that in the second electrolytic solution 204 be replaced with membrane-impermeant negative ions, such as $SO_4^{2-}$, Methanesulfonate, gluconate, glutamate, or aspartate. It is preferable that the second electrolytic solution 204 be refrigerated at −20° C. to prevent microorganisms from multiplying. It is preferable that positive ions in the second electrolytic solution 204 be replaced with membrane-impermeant organic bases. It is preferable that the positive ions in the second electrolytic solution 204 be replaced with tetraechylammonium or N-methyl-D-glucamine. It is preferable that EGTA contained in the second electrolytic solution 204 be replaced with BAPTA. The second electrolytic solution 204 may contain ATP. In order to maintain the function of the receptor, the second electrolytic solution 204 may contain 0.1 to 0.3 mM of GTP.

It is preferable that the viscosity of the second electrolytic solution 204 be not lower than 1.3 mPa·s and not higher than 200 mPa·s. It is preferable that the viscosity of the second electrolytic solution 204 be the same as that of the first electrolytic solution 201. However, the viscosity of the second electrolytic solution 204 may be different from that of the first electrolytic solution 201. It is preferable that the second electrolytic solution 204 have flowability in order to reduce the voltage drop and increase the ion conductance. It is preferable that the second electrolytic solution 204 be a liquid form or a semiliquid form.

The viscosity of the second electrolytic solution 204 is adjusted in the same manner as the first electrolytic solution 201.

It is preferable that the viscosity of the second electrolytic solution 204 be higher than the viscosity (1.0 mPa·s) of pure water having a temperature of 20° C.

In order to reduce the voltage drop, it is preferable that the electrical resistivity of the second electrolytic solution 204 be not lower than 1 μΩm and not higher than 100 kΩm, and it is more preferable that the electrical resistivity of the second electrolytic solution 204 be not lower than 1 mΩm and not higher than 10 Ωm. It is preferable that the second electrolytic solution 204 be transparent such that the artificial lipid membrane can be observed. However, the second electrolytic solution 204 may be opaque.

It is preferable that the amount of the second electrolytic solution 204 added to the second chamber 105 be not smaller than 10 pl and not larger than 200 μl, and it is more preferable that the amount of the second electrolytic solution 204 added to the second chamber 105 be not smaller than 1 nl and not larger than 200 μl. It is most preferable that the second electrolytic solution 204 remain still. However, the second electrolytic solution 204 may be flowing. It is preferable that in a case where the second electrolytic solution 204 is flowing, the amount of the second electrolytic solution 204 which practically involves the formation of the artificial lipid membrane be within the above range. After the second electrolytic solution 204 is added to the second chamber 105, the surplus second electrolytic solution 204 may be discharged to adjust the amount of the second electrolytic solution 204 in the second chamber 105.

It is preferable that the second electrolytic solution 204 be added to the second chamber 105 by using a pipette. However, the second electrolytic solution 204 may be added to the second chamber 105 by using a tube, a flow channel, a dropper, or a syringe. The second electrolytic solution 204 may be added to the second chamber 105 continuously or intermittently. The second electrolytic solution 204 may be added to the second chamber 105 as liquid droplets. As a method for adding the liquid droplets of the second electrolytic solution 204, the ink-jet method, the minute liquid droplet applying method, the dot impact method, the electrostatic spraying method, the ultrasound method, or the minute liquid droplet applying method may be used. It is most preferable that the ink-jet method be the piezo type. However, the ink-jet method may be the thermal type.

The second electrolytic solution 204 is added manually, semi-manually, or automatically. It is preferable that the adding time of the second electrolytic solution 204 be not shorter than 1 microsecond and not longer than 10 seconds, and it is more preferable that the adding time of the second electrolytic solution 204 be not shorter than 1 microsecond and not longer than 1 second. The adding speed of the second electrolytic solution 204 may be constant or may change in the second electrolytic solution adding step.

In order to suppress drying of the second electrolytic solution 204, it is preferable that the second electrolytic solution 204 be maintained at room temperature in the second electrolytic solution adding step. It is preferable that the second electrolytic solution 204 be maintained at a temperature of not lower than 0° C. and not higher than 40° C., and it is more preferable that the second electrolytic solution 204 be maintained at a temperature of not lower than 10° C. and not higher than 30° C. It is preferable that the relative humidity around the artificial lipid membrane forming apparatus 100 be maintained to be not lower than 50% and not higher than 100%.

It is preferable that dusts and impurities contained in the second electrolytic solution 204 be removed with a membrane filter.

It is preferable that the second electrolytic solution 204 be added to the second chamber 105 by the capillary force, the gravity, the surface tension, or the centrifugal force in the second electrolytic solution adding step.

In the second electrolytic solution adding step, the termination of the addition of the second electrolytic solution 204 to the second chamber 105 may be detected. The termination of the addition may be detected by observation using an optical microscope or may be detected by providing a plurality of electrodes at the second chamber 105 and measuring the electric conductivity. It is preferable that the second electrolytic solution 204 be added to the second chamber 105 in the second electrolytic solution adding step until the second electrolytic solution 204 exceeds the upper end of the artificial lipid membrane forming portion 103. It is preferable that the second electrolytic solution 204 be added to the second chamber 105 in the second electrolytic solution adding step.

It is most preferable that the second electrolytic solution 204 be an uniform electrolytic solution having a single viscosity. The second electrolytic solution 204 may be an electrolytic solution that is a combination of a plurality of electrolytic solutions, each having the viscosity of not lower than 1.3 mPa·s and not higher than 200 mPa·s. The viscosity of the second electrolytic solution 204 may have gradient. The gradient of the viscosity of the second electrolytic solution 204 may be continuous or discontinuous.

The second electrolytic solution 204 is minute in amount. Therefore, if the viscosity of the second electrolytic solution 204 is too low, the second electrolytic solution 204 evaporates in some cases while providing a cover or a stopple on the opening of the first chamber 104 or the second chamber 105 or attaching a film to the opening. On this account, the operations require extra attention.

Step E: Artificial Lipid Membrane Forming Step

FIG. 5(c) shows the artificial lipid membrane forming step. In the artificial lipid membrane forming step, an artificial lipid membrane 205 is formed at the artificial lipid membrane forming portion 103. It is most preferable that the artificial lipid membrane 205 be a lipid bilayer. However, the artificial lipid membrane 205 may contain a monomolecular film or a multiplayer, such as a tetralayer or a hexalayer. It is preferable that the surplus organic solvent and the surplus lipids 203 be removed from the thin film of the lipid solution 202 in the artificial lipid membrane forming step by the pressure of the first electrolytic solution 201 and the pressure of the second electrolytic solution 204 or by an external pressure. It is preferable that the surplus organic solvent and the surplus lipids 203 be removed along an outer peripheral surface of the dividing wall 102. In order to accelerate removal of the organic solvent and the lipids 203 and prevent the organic solvent and the lipids 203 from being removed beyond necessity, a structure, such as a groove structure or a concave-convex structure, configured to control microfluids may be provided on at least one of outer peripheral surfaces of the dividing wall 102.

In order to remove the surplus organic solvent and the surplus lipids 203, the solution levels of the first electrolytic solution 201 and/or the second electrolytic solution 204 may be caused to go up and down in the artificial lipid membrane forming step.

In order to remove the surplus organic solvent and the surplus lipids 203, a voltage may be applied to both surfaces of the artificial lipid membrane in the artificial lipid membrane forming step. It is preferable that the voltage applied to both surfaces of the artificial lipid membrane 205 be not lower than 1 mV and not higher than 1 V, and it is more preferable that the voltage applied to both surfaces of the artificial lipid membrane 205 be not lower than 50 mV and not higher than 200 mV. The applied voltage may be a DC voltage or an AC voltage.

The artificial lipid membrane forming step may comprise a step of detecting the formation of the artificial lipid membrane 205. The formation of the artificial lipid membrane 205 may be detected by observation using the optical microscope or by measurement of absorbance of the artificial lipid membrane 205. Moreover, the formation of the artificial lipid membrane 205 may be detected by providing a plurality of electrodes 108 at the first chamber 104 and the second chamber 105 and measuring membrane resistance, membrane capacity, membrane current, or the other electrical characteristic of the artificial lipid membrane 205.

The first electrolytic solution 201 is minute in amount. Therefore, if the viscosity of the first electrolytic solution 201 is too low, the first electrolytic solution 201 evaporates in some cases in the artificial lipid membrane forming step. On this account, the operations require extra attention. The same is true for the second electrolytic solution 204.

It is preferable that the electrode 108 be a nonpolarizable electrode. It is preferable that the material of the electrode 108 be an electrode material suitable for electrochemical measurements. The material of the electrode 108 may be a single metal, such as Au, Pt, or Ag.

It is most preferable that the electrode 108 be an Ag/AgCl electrode. However, the electrode 108 may be an electrode using an inorganic material, such as a saturated calomel electrode, a hydrogen electrode, a carbon electrode, a graphite electrode, or a carbon nanotube electrode. The electrode 108 may be a field-effect transistor (FET) or may be a gate electrode, source electrode, or drain electrode of the field-effect transistor. The electrode 108 may be an ion-sensitive field-effect transistor (ISFET) or a gel electrode.

A chemical substance, such as an ion, an enzyme, a reaction product, or a substrate contained in the first electrolytic solution 201 or the second electrolytic solution 204 may be measured by using the electrode 108.

It is preferable that the electrode 108 have a wire shape. However, the electrode 108 may have a thin film shape, a rod shape, a flat plate shape, a columnar shape, a quadrangular prism shape, a polygonal column shape, a coil shape, or a mesh shape. In light of handleability, it is preferable that in a case where the electrode 108 has the wire shape, the length of the electrode 108 be not smaller than 10 nm and not larger than 1 cm. It is preferable that in a case where the electrode 108 has the wire shape, the diameter of the electrode 108 be not smaller than 10 nm and not larger than 1 cm.

In a case where the electrode 108 has a flat plate shape, it is preferable that each of the length, width, and thickness of the electrode 108 be not smaller than 10 nm and not larger than 1 cm. In a case where the electrode 108 has a thin film shape, it is preferable that each of the length and width of the electrode 108 be not smaller than 10 nm and not larger than 1 cm. In a case where the electrode 108 has the thin film shape, it is preferable that the thickness of the electrode 108 be not smaller than 10 nm and not larger than 100 μm, and it is more preferable that the thickness of the electrode 108 be not smaller than 50 nm and not larger than 1 μm.

It is preferable that the electrode 108 be provided on the inner wall of the container 101. However, the electrode 108 may be provided on a side wall or bottom portion of the container 101. The electrode 108 may be provided in the artificial lipid membrane forming apparatus 100 so as not to contact the inner wall of the container 101.

One electrode 108 may be provided, or a plurality of electrodes 108 may be provided. In a case where the plurality of electrodes 108 are provided, all the electrodes 108 may be constituted by the same material or may be constituted by different materials. In a case where the plurality of electrodes 108 are provided, all the electrode 108 may be the same in shape as one another or different in shape from one another. In a case where the plurality of electrodes 108 are provided, all the electrodes 108 may be the same in size as one another or different in size from one another.

In accordance with such configuration and operation procedure, since the first electrolytic solution 201 and the second electrolytic solution 204 are high in viscosity, the first electrolytic solution 201 and the second electrolytic solution 204 can be prevented from leaking through the openings of the inlet 24 and outlet 304 to the outside of the first chamber 104 and the outside of the second chamber 105. As a result, the periphery of the artificial lipid membrane forming apparatus 100 can be prevented from being contaminated by the electrolytic solution. Further, since a minute amount of first electrolytic solution 201 and a minute amount of second electrolytic solution 204 are prevented from rapidly evaporating, the artificial lipid membrane 205 can be stably formed.

In Embodiment 1, as shown in FIG. 1, it is preferable that the artificial lipid membrane forming apparatus 100 be placed on a horizontal surface to operate. However, the artificial lipid membrane forming apparatus 100 may be placed on an inclined surface to operate. This is because the first electrolytic solution 201 and the second electrolytic solution 204 are high in viscosity, so that even if the artificial lipid membrane forming apparatus 100 is placed on the inclined surface, the first electrolytic solution 201 and the second electrolytic solution 204 are prevented from leaking to the outside of the first chamber 104 and the outside of the second chamber 105.

In the middle of the step of forming the artificial lipid membrane 205, the artificial lipid membrane forming apparatus 100 may receive vibrations, be inclined, or be turned over. In addition, after the artificial lipid membrane 205 is formed, the artificial lipid membrane forming apparatus 100 may receive vibrations, be inclined, or be turned over. These troubles tend to occur especially in a case where the artificial lipid membrane forming apparatus 100 is compact.

However, in Embodiment 1, the first electrolytic solution 201 and the second electrolytic solution 204 are high in viscosity, so that even if the artificial lipid membrane forming apparatus 100 receives vibrations, is inclined, or is turned over, the first electrolytic solution 201 and the second electrolytic solution 204 are prevented from leaking to the outside of the first chamber 104 and the outside of the second chamber 105.

Figure 6:
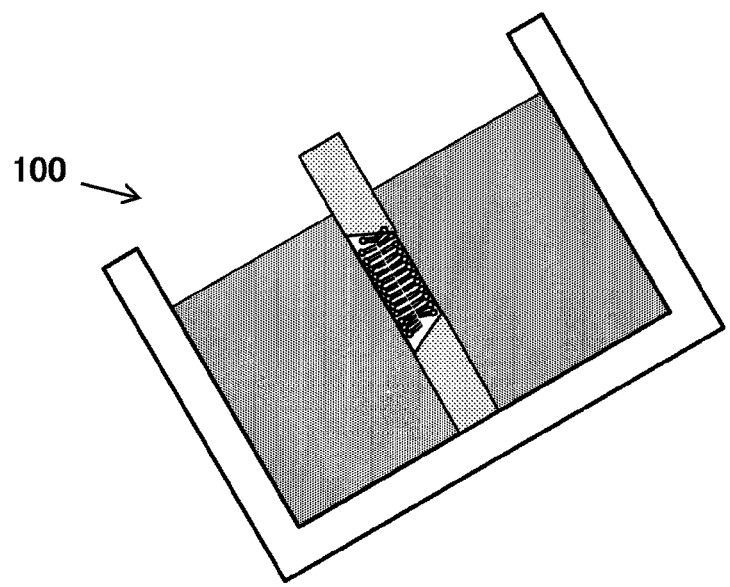
FIG. 6 shows a state where the artificial lipid membrane forming apparatus of Embodiment 1 is inclined.
Figure 7:
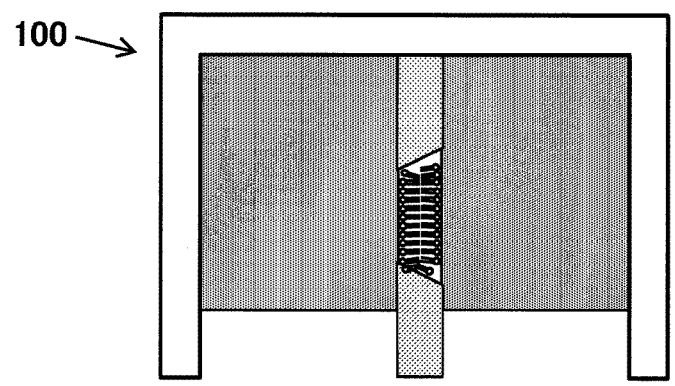
FIG. 7 shows a state where the artificial lipid membrane forming apparatus of Embodiment 1 is placed upside down.

As shown in FIG. 6, the artificial lipid membrane forming apparatus 100 can operate in an inclined state. As shown in FIG. 7, the artificial lipid membrane forming apparatus 100 can also operate in an upside-down state of the state shown in FIG. 1. The artificial lipid membrane forming apparatus 100 may remain still, be moving, or be vibrating.

Figure 8:
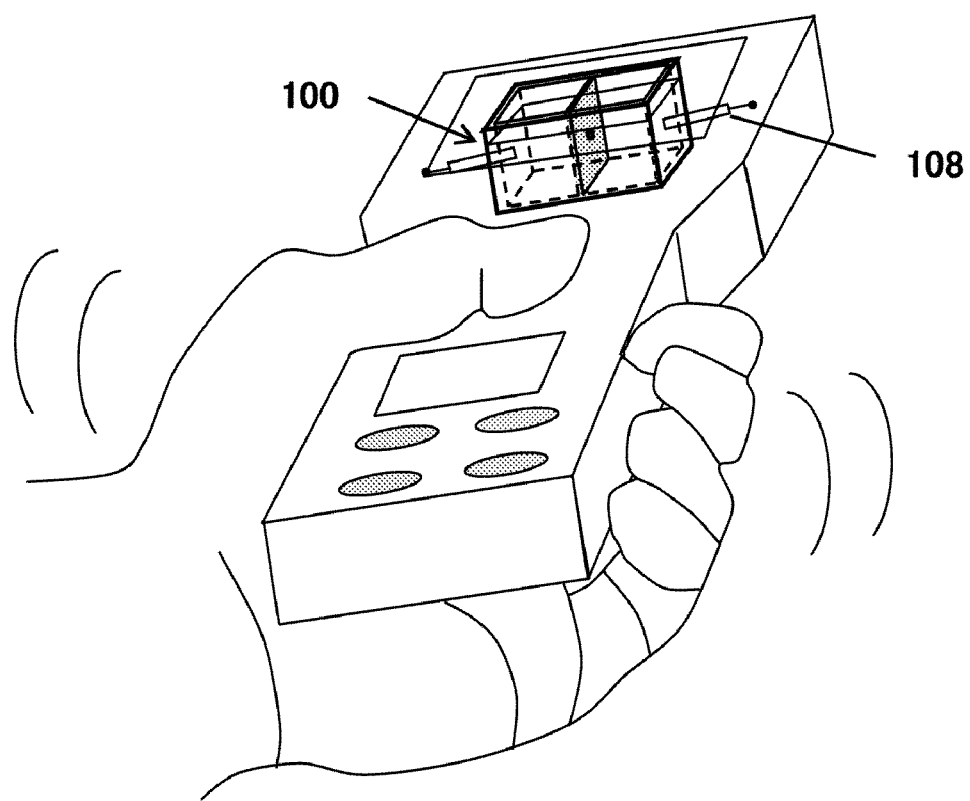
FIG. 8 shows a state where the artificial lipid membrane forming apparatus of Embodiment 1 is held in a hand of an operator.

As shown in FIG. 8, the artificial lipid membrane forming apparatus 100 may be held in a hand of an operator to operate. This is because the first electrolytic solution 201 and the second electrolytic solution 204 are high in viscosity, so that as shown in FIG. 8, even if the hand of the operator shakes, the first electrolytic solution 201 and the second electrolytic solution 204 can be prevented from leaking. As shown in FIG. 8, the artificial lipid membrane forming apparatus 100 may be incorporated in a part of a mobile terminal.

In Embodiment 1, the lipid solution adding step may be carried out after the first electrolytic solution adding step and the second electrolytic solution adding step. To be specific, the conventional bubble spraying method, pipetting, or brush coating may be applied to the present embodiment. In the present embodiment, the first electrolytic solution adding step and the lipid solution adding step may be simultaneously carried out, and the second electrolytic solution adding step and the lipid solution adding step may be simultaneously carried out. To be specific, the conventional attaching method may be applied to the present embodiment.

In Embodiment 1, it is preferable that a series of steps from the first electrolytic solution adding step to the artificial lipid membrane forming step be carried out at a temperature of not lower than 20° C. and not higher than 60° C., and it is more preferable that the series of steps be carried out at a temperature of not lower than 25° C. and not higher than 40° C.

Biosensors can be manufactured by using the artificial lipid membrane forming method of Embodiment 1. It is preferable that the biosensor using the artificial lipid membrane forming method of the present embodiment be utilized for the detection of an organic compound. It is preferable that the organic compound be a volatile organic compound, a biomolecule, a diagnostic marker, a protein, a peptide, a base, or a metabolic substance. It is preferable that the viscosity of the electrolytic solution be adjusted since an effect of trapping or concentrating detected substances of the biosensor can be expected.

As compared to a conventional solid gel, the detected substances rapidly disperse in the electrolytic solution having the flowability. Therefore, the biosensor using the electrolytic solution is expected to perform quicker sensing than the biosensor using the solid gel. It is preferable that the biosensor using the artificial lipid membrane forming method of Embodiment 1 be applied to an analyzing device. Examples of the analyzing device are clinical examination analyzing devices, electrochemical analyzing devices, gas analyzing devices, taste analyzing devices, neurophysiological analyzers, ion channel analyzers, ion channel function analyzers, and drug screening devices. The artificial lipid membrane forming method of Embodiment 1 may be applied to chemical substance detecting devices, biomolecule analyzing devices, air pollutant analyzing devices, water pollutant analyzing devices, residual agricultural chemical analyzing devices, food composition analyzing devices, drug analyzing devices, drinking determining devices, smoking determining devices, explosive searching devices, gas leakage detectors, fire alarms, missing person searching devices, personal identification devices, air cleaning devices, lifestyle disease diagnostic devices, urine analyzing devices, body fluid analyzing devices, breath analyzing devices, blood analyzing devices, blood gas analyzing devices, and stress measuring devices.

Embodiment 2

Hereinafter, Embodiment 2 of the present invention will be explained in reference to the drawings.

Step A: Preparing Step

Figure 9:
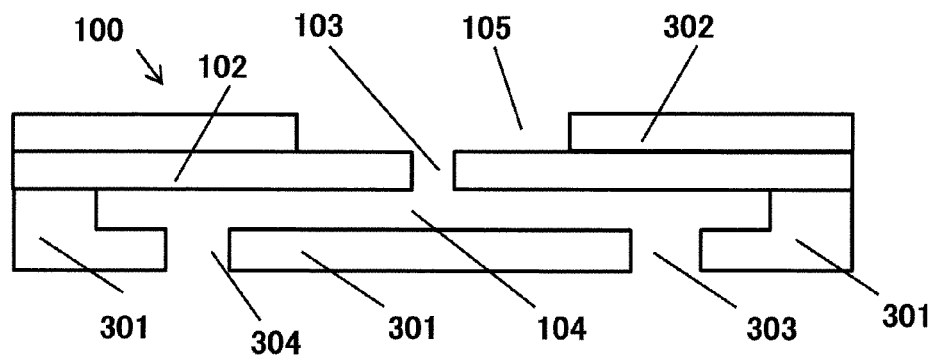
FIG. 9 shows a cross-sectional view of the artificial lipid membrane forming apparatus of Embodiment 2.
Figure 10:
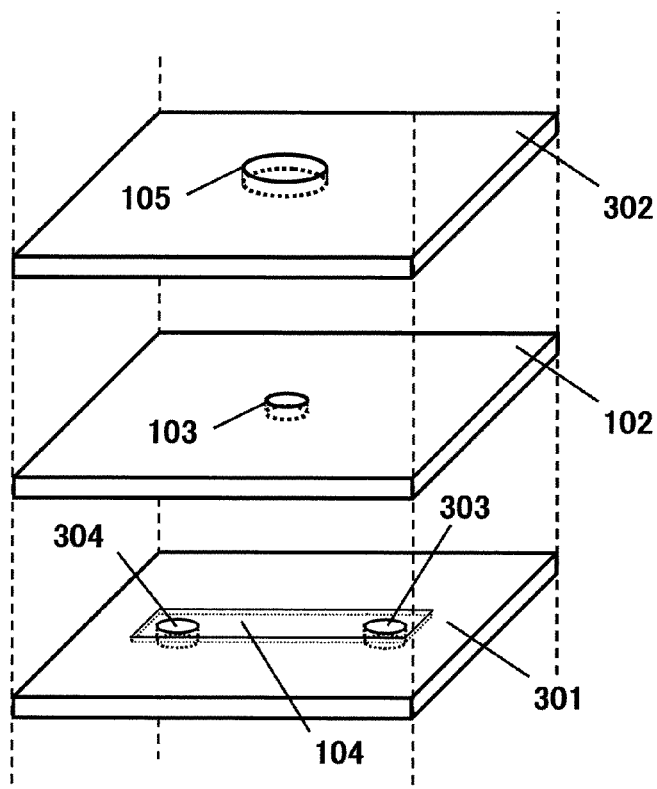
FIG. 10 shows an exploded oblique projection view of the artificial lipid membrane forming apparatus of Embodiment 2.

FIGS. 9 and 10 respectively show a cross-sectional view and exploded oblique projection view of the artificial lipid membrane forming apparatus 100 of Embodiment 2 of the present invention. In Embodiment 2, the same reference signs are used for the same components as in Embodiment 1, and detailed explanations thereof are omitted.

A largest difference between Embodiment 2 and Embodiment 1 is that in Embodiment 2, the artificial lipid membrane 205 is formed with the µTAS technique. Specifically, the largest difference between Embodiment 2 and Embodiment 1 is that in Embodiment 2, the first chamber 104 and/or the second chamber 105 are micro passages or micro holes. Since the first chamber 104 and the second chamber 105 are miniaturized with the µTAS technique, a ratio of a contact area S between the electrolytic solution and the chamber to the amount V of electrolytic solution, that is, an S/V value increases. As a result, the first electrolytic solution 201 and the second electrolytic solution 204 can be further prevented from leaking from the first chamber 104 and the second chamber 105.

Any of the materials, each of which can be used as the material of the container 101, may be used as the material of a first substrate 301. It is most preferable that the material of the first substrate 301 be an insulator.

It is preferable that at least a part of the outer peripheral surface of the first substrate 301 be hydrophilic. In order to give the hydrophilic property to at least the part of the outer peripheral surface of the first substrate 301, at least the part of the outer peripheral surface of the first substrate 301 may be subjected to an oxygen plasma treatment or may be covered with a hydrophilic material.

It is preferable that the material of the first substrate 301 be transparent such that the artificial lipid membrane 205 can be observed. However, the material of the first substrate 301 may be opaque.

It is most preferable that the first substrate 301 have a flat plate shape. However, the first substrate 301 may have a disc shape, a trapezoidal shape, a polygonal shape, a columnar shape, or a prismatic shape.

It is preferable that the first substrate 301 be molded by machine work. It is preferable that the machine work be injection molding, extrusion molding, compression molding, hollow molding, cutting operation, molding, sand blasting, dry etching, wet etching, nanoimprint, milling, photocuring, lithography, or hot embossing. It is also preferable that the first substrate 301 be processed with a semiconductor process.

The dividing wall 102 is sandwiched between the first substrate 301 and a second substrate 302. The dividing wall 102 of Embodiment 2 may be made of the same material as the dividing wall 102 of Embodiment 1.

As with Embodiment 1, it is preferable that the artificial lipid membrane forming portion 103 have a tapered shape as shown in FIG. 2. The tapered shape may narrow down toward the first chamber 104 or may narrow down toward the second chamber 105. As shown in FIGS. 9 and 10, the artificial lipid membrane forming portion 103 may be a through hole having a constant diameter.

The first chamber 104 is provided at a part of the first substrate 301. It is preferable that the first chamber 104 be provided between the first substrate 301 and the dividing wall 102, and it is most preferable that the first chamber 104 be formed by the first substrate 301 and the dividing wall 102. In light of the operability, it is preferable that the capacity of the first chamber 104 be not smaller than 1 pl and not larger than 1 ml, and it is more preferable that the capacity of the first chamber 104 be not smaller than 10 pl and not larger than 200 µl. It is preferable that the first chamber 104 comprise a first inlet 303 through which the electrolytic solution is added and the outlet 304. It is preferable that the first chamber 104 be a flow channel. The first chamber 104 may be a micro hole, a capillary, a tube, or a reservoir. The first chamber 104 may be connected to an electrolytic solution reservoir through a passage. The capacity of the electrolytic solution reservoir may be or may not be included in the capacity of the first chamber 104. A cover or a stopple may be provided on the opening of the first chamber 104, or a film may be attached to the opening of the first chamber 104.

In order to increase the surface area to prevent the electrolytic solution from leaking, it is preferable that a holding structure be mounted in the first chamber 104. It is preferable that the holding structure be a pillar, a porous body, a ball, a bead, a dot, a sponge, a fiber, or a foam. The holding structure may be a nano pillar, a micro pillar, a porous metal, a porous ceramic, a micro bead, a nano bead, a nano foam, a porous silicon, a porous silica, or a porous alumina.

Any of the materials, each of which can be used as the material of the container 101, may be used as the material of the holding structure. A part of the surface of the holding structure may be covered with a thin film made of a material different from the material of the holding structure. The thin film covering the surface of the holding structure is the same as the dividing wall 102.

The holding structure may be formed at the same time as the formation of the first chamber 104 or may be formed after the formation of the first chamber 104. The holding structure may be formed in advance and is then provided in the first chamber 104.

As with the holding structure, any of the materials, each of which can be used as the material of the container 101, may be used as the material of the second substrate 302. It is most preferable that the material of the second substrate 302 be an insulator.

It is preferable that at least a part of the outer peripheral surface of the second substrate 302 is hydrophilic. In order to give the hydrophilic property to at least the part of the outer peripheral surface of the second substrate 302, at least the part of the outer peripheral surface of the second substrate 302 may be subjected to an oxygen plasma treatment or may be covered with a hydrophilic material.

It is preferable that the material of the second substrate 302 be transparent such that the artificial lipid membrane 205 can be observed. However, the material of the second substrate 302 may be opaque.

It is most preferable that the second substrate 302 have a flat plate shape. However, the second substrate 302 may have a disc shape, a trapezoidal shape, a polygonal shape, a columnar shape, or a prismatic shape.

The second chamber 105 is provided on an opposite side of the first chamber 104 via the dividing wall 102. It is preferable that the second chamber 105 be provided between the second substrate 302 and the dividing wall 102, and it is most preferable that the second chamber 105 be formed by the second substrate 302 and the dividing wall 102. The volume of the second chamber 105 is the same as in Embodiment 1. It is preferable that the second chamber 105 comprises an inlet through which the electrolytic solution is added. It is preferable that the second chamber 105 be a flow channel. However, the second chamber 105 may be a micro hole, a capillary, a tube, or a reservoir. The second chamber 105 may be connected to an electrolytic solution reservoir through a passage. The capacity of the electrolytic solution reservoir may be or may not be included in the capacity of the second chamber 105. A cover or a stopple may be provided on the opening of the second chamber 105, or a film may be attached to the opening of the second chamber 105.

In order to increase the surface area to prevent the electrolytic solution from leaking, it is preferable that the same holding structure as the first chamber 104 be mounted in the second chamber 105. The holding structure may be formed at the same time as the formation of the second chamber 105 or may be formed after the formation of the second chamber 105. The holding structure may be formed in advance and is then provided in the second chamber 105.

Figure 11:
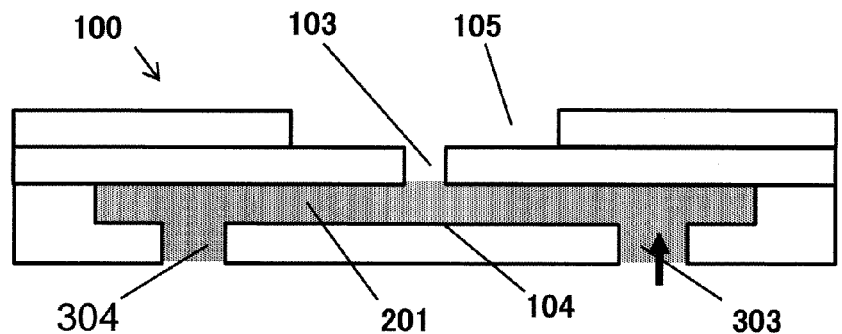
FIG. 11 shows steps from the first electrolytic solution adding step to a second electrolytic solution adding step in Embodiment 2.
Figure 11:
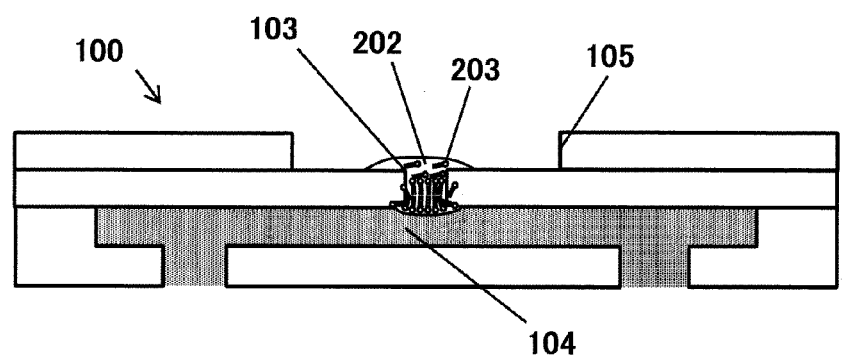
Figure 11:
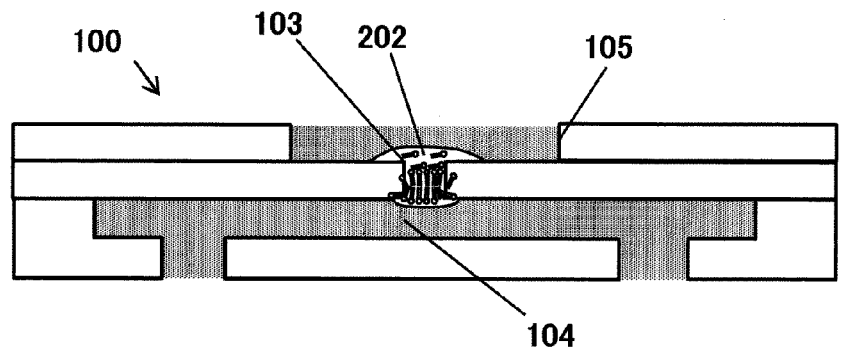
Figure 12:
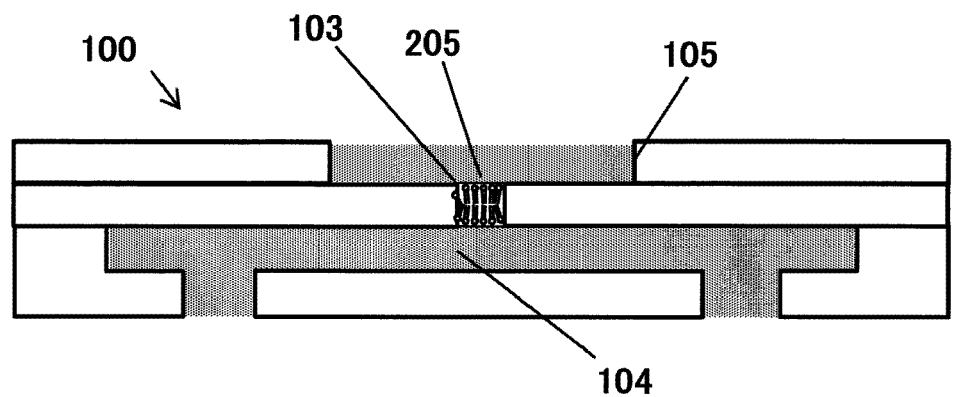
FIG. 12 shows the artificial lipid membrane forming step of Embodiment 2.

Next, a procedure of forming the artificial lipid membrane will be explained. FIGS. 11 and 12 show diagrams of the operations of the artificial lipid membrane forming apparatus 100 of Embodiment 2 of the present invention. In FIGS. 11 and 12, the same reference signs are used for the same components as in FIGS. 9 and 10, and explanations thereof are omitted.

Step B: First Electrolytic Solution Adding Step

FIG. 11(a) shows the first electrolytic solution adding step. In the first electrolytic solution adding step, the first electrolytic solution 201 is added through the first inlet 303 to the first chamber 104, and the first chamber 104 is filled with the first electrolytic solution 201. The surplus first electrolytic solution 201 may be discharged through the outlet 304. The outlet 304 may be used to release air bubbles in the first chamber 104.

As the first electrolytic solution 201, the same electrolytic solution as in Embodiment 1 may be used. The first electrolytic solution 201 has the same viscosity and electrical resistivity as in Embodiment 1. The viscosity of the first electrolytic solution 201 may be adjusted in the same manner as in Embodiment 1.

The method for adding the first electrolytic solution 201 through the first inlet 303 to the first chamber 104 is the same as in Embodiment 1. The temperature of the first electrolytic solution 201 and the relative humidity around the artificial lipid membrane forming apparatus 100 are the same as in Embodiment 1.

The termination of the addition of the first electrolytic solution 201 to the first chamber 104 may be detected in the same manner as in Embodiment 1.

Step C: Lipid Solution Adding Step

FIG. 11(b) shows the lipid solution adding step. In the lipid solution adding step, the lipid solution 202 is added to the artificial lipid membrane forming portion 103. It is preferable that in the lipid solution adding step, the lipid solution 202 be added from the second chamber 105 side.

As the lipid solution 202, the same lipid solution as in Embodiment 1 may be used. As with Embodiment 1, the lipid solution 202 is added to the artificial lipid membrane forming portion 103. As with Embodiment 1, the biological membrane protein, the secretory protein, or the polypeptide may be introduced to the artificial lipid membrane.

The termination of the addition of the lipid solution 202 to the artificial lipid membrane forming portion 103 may be detected in the same manner as in Embodiment 1.

Step D: Second Electrolytic Solution Adding Step

FIG. 11(c) shows the second electrolytic solution adding step. In the second electrolytic solution adding step, the second electrolytic solution 204 is added to the second chamber 105.

As the second electrolytic solution 204, the same electrolytic solution as in Embodiment 1 may be used. The second electrolytic solution 204 has the same viscosity and electrical resistivity as in Embodiment 1. The viscosity of the second electrolytic solution 204 may be adjusted in the same manner as in Embodiment 1.

The method for adding the second electrolytic solution 204 to the second chamber 105 is the same as in Embodiment 1. The temperature of the second electrolytic solution 204 and the relative humidity around the artificial lipid membrane forming apparatus 100 are the same as in Embodiment 1.

The termination of the addition of the second electrolytic solution 204 to the second chamber 105 may be detected in the same manner as in Embodiment 1.

Step E: Artificial Lipid Membrane Forming Step

FIG. 12 shows the artificial lipid membrane forming step. In the artificial lipid membrane forming step, the artificial lipid membrane 205 is formed at the artificial lipid membrane forming portion 103. The artificial lipid membrane 205 is the same as in Embodiment 1. The artificial lipid membrane forming step of Embodiment 2 is the same as in Embodiment 1.

In Embodiment 2, as shown in FIG. 12, it is preferable that the artificial lipid membrane forming apparatus 100 be placed on a horizontal surface to operate. However, the artificial lipid membrane forming apparatus 100 may be placed on an inclined surface to operate. This is because the first electrolytic solution 201 and the second electrolytic solution 204 are high in viscosity, so that even if the artificial lipid membrane forming apparatus 100 is placed on the inclined surface, the first electrolytic solution 201 and the second electrolytic solution 204 are prevented from leaking to the outside of the first chamber 104 and the outside of the second chamber 105.

Figure 13:
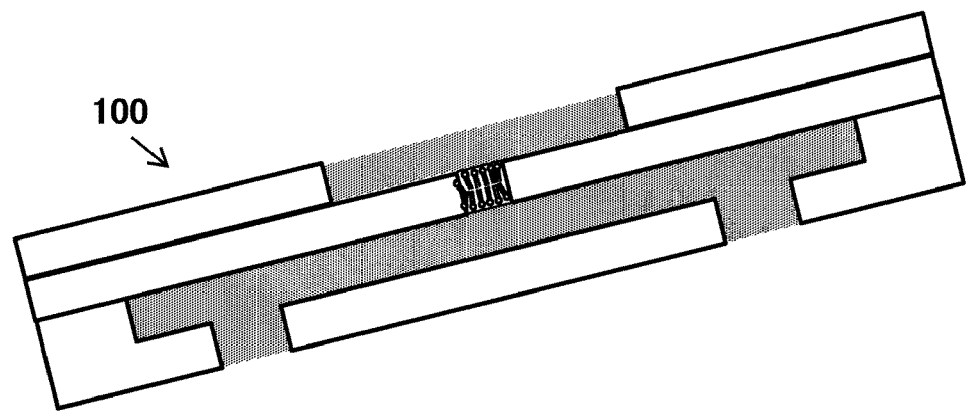
FIG. 13 shows a state where the artificial lipid membrane forming apparatus of Embodiment 2 is inclined.
Figure 14:
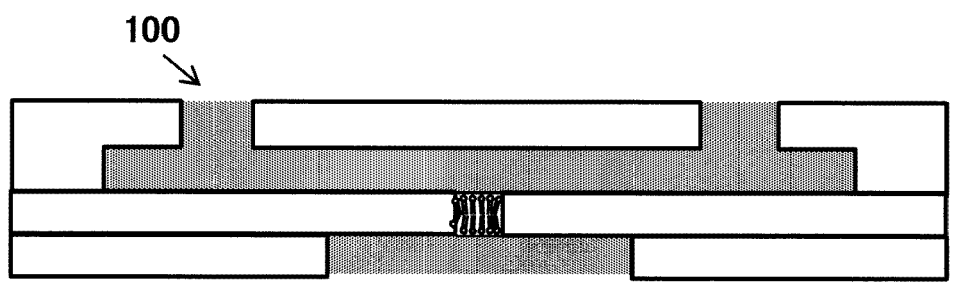
FIG. 14 shows a state where the artificial lipid membrane forming apparatus of Embodiment 2 is placed upside down.
Figure 15:
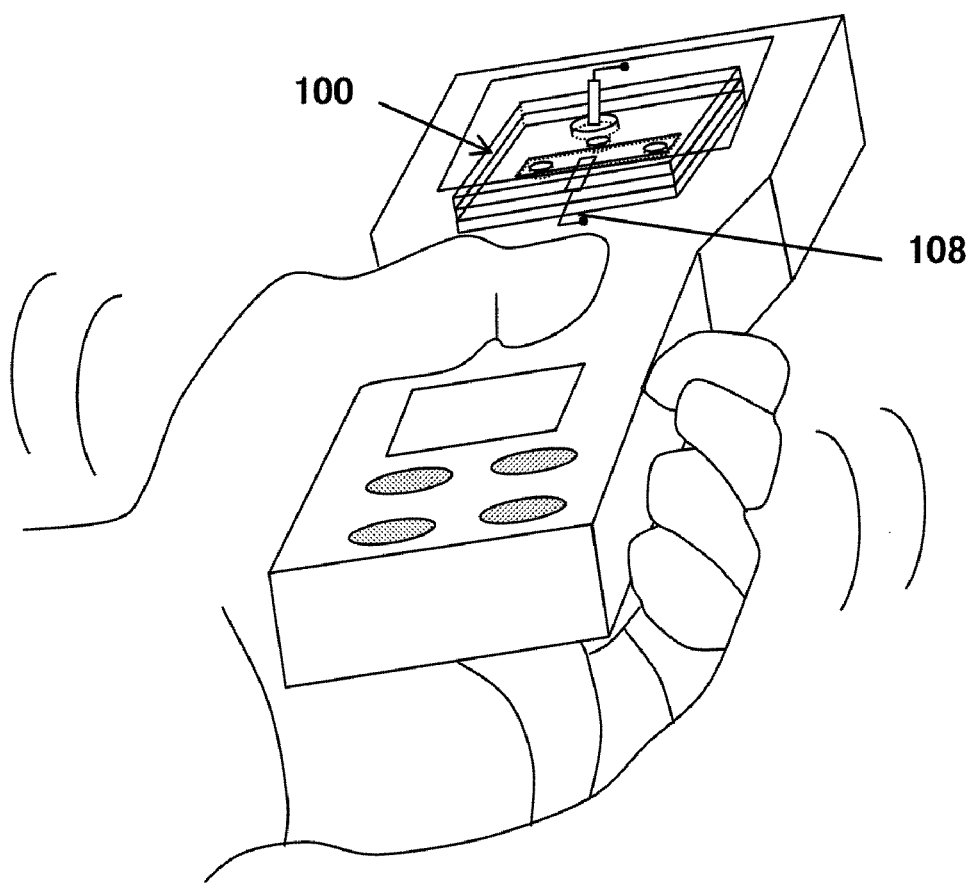
FIG. 15 shows a state where the artificial lipid membrane forming apparatus of Embodiment 2 is held in a hand of an operator.

Even in a case where the artificial lipid membrane forming apparatus 100 receives vibrations, is inclined, or is turned over, the first electrolytic solution 201 and the second electrolytic solution 204 can be prevented from leaking to the outside of the first chamber 104 and the outside of the second chamber 105. For example, as shown in FIG. 13, the artificial lipid membrane forming apparatus 100 can operate in an inclined state. As shown in FIG. 14, the artificial lipid membrane forming apparatus 100 can also operate in an upside-down state as shown in FIG. 12. The artificial lipid membrane forming apparatus 100 may remain still, be moving, or be vibrating. As shown in FIG. 15, the artificial lipid membrane forming apparatus 100 may be held in a hand of an operator. This is because the first electrolytic solution 201 and the second electrolytic solution 204 are high in viscosity, so that as shown in FIG. 15, even if the hand of the operator shakes, the first electrolytic solution 201 and the second electrolytic solution 204 can be prevented from leaking. As shown in FIG. 15, the artificial lipid membrane forming apparatus 100 may be incorporated in a part of a mobile terminal.

In Embodiment 2, the lipid solution adding step may be carried out after the first electrolytic solution adding step and the second electrolytic solution adding step. To be specific, the conventional bubble spraying method, pipetting method, or brush coating may be applied to the present embodiment. In the present embodiment, the first electrolytic solution adding step and the lipid solution adding step may be simultaneously carried out, and the second electrolytic solution adding step and the lipid solution adding step may be simultaneously carried out. To be specific, the conventional attaching method may be applied to the present embodiment.

Figure 16:
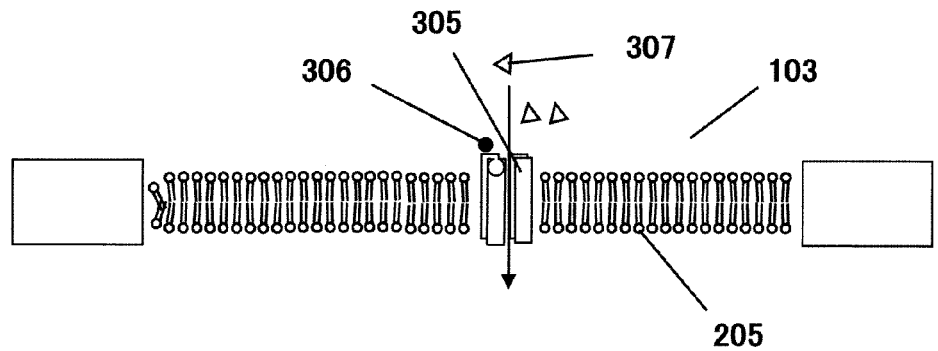
FIG. 16 schematically shows a state where membrane proteins are implanted in an artificial lipid membrane in Embodiment 2.
Figure 16:
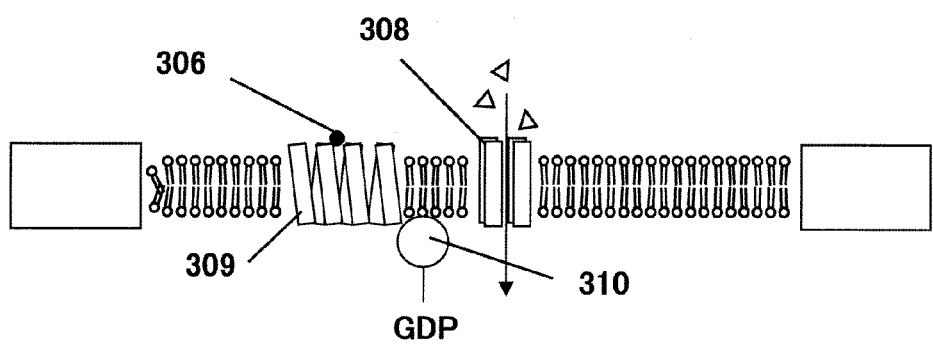
Figure 16:
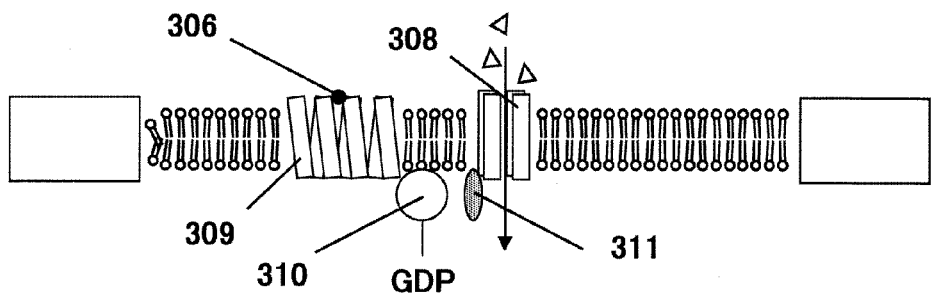

In Embodiment 2, the membrane protein may be implanted in the artificial lipid membrane 205. FIGS. 16(a) to 16(c) schematically show a state where the membrane protein is implanted in the artificial lipid membrane 205. It is also preferable that a receptor channel 305 be implanted in the artificial lipid membrane 205. FIG. 16(a) schematically shows a state where the receptor channel 305 is implanted in the artificial lipid membrane 205 formed at the artificial lipid membrane forming portion 103. The receptor channel 305 opens by direct ligand binding to a channel protein as a trigger. FIG. 16(a) schematically shows a state where a ligand 306 binds to the receptor channel 305. An ion 307 passes through the open receptor channel 305.

It is also preferable that a G protein 310 be implanted in the artificial lipid membrane 205. FIG. 16(b) schematically shows a state where a channel 308, a receptor protein 309, and the G protein 310 are implanted in the artificial lipid membrane 205 formed at the artificial lipid membrane forming portion 103. The channel 308 is triggered by an active GTP binding protein (G protein 310) produced by the ligand binding to the independent receptor protein 309.

It is preferable that a second messenger control channel be implanted in the artificial lipid membrane 205. FIG. 16(c) schematically shows a state where the channel 308, the receptor protein 309, the G protein 310, and an enzyme 311 are implanted in the artificial lipid membrane 205 formed at the artificial lipid membrane forming portion 103. The channel 308 is activated by a second messenger produced after the activation of the G protein 310.

The membrane protein implanted in the artificial lipid membrane 205 may be an integral membrane protein or may be a superficial membrane protein. The membrane protein implanted in the artificial lipid membrane 205 may be a transmembrane protein or may be a single-pass transmembrane protein. The membrane protein implanted in the artificial lipid membrane 205 may be a receptor, an ion channel, or a G protein.

It is preferable that the receptor implanted in the artificial lipid membrane 205 be a transmembrane receptor or an intracellular receptor. The receptor implanted in the artificial lipid membrane 205 may be a metabolic receptor or may be an ion channel receptor. It is preferable that the receptor implanted in the artificial lipid membrane 205 be a G protein conjugated receptor (GPCR). The receptor implanted in the artificial lipid membrane 205 may be a muscarinic acetylcholine receptor, an adenosine receptor, an adrenergic receptor, a GABA receptor, an angiotensin receptor, a cannabinoid receptor, a cholecystokinin receptor, a dopamine receptor, a glucagon receptor, a histamine receptor, an olfactory receptor, an opioid receptor, a rhodopsin, a secretin receptor, a serotonin receptor, a somatostatin receptor, a gastrin receptor, a P2Y receptor, a tyrosine kinase receptor, an erythropoietin receptor, an insulin receptor, a cell growth factor receptor, a cytokine receptor, a guanylate cyclase receptor, a nicotinic acetylcholine receptor, a glycine receptor, a glutamate receptor, an inositol trisphosphate receptor, a ryanodine receptor, or a P2X receptor.

In Embodiment 2, it is most preferable that the G protein implanted in the artificial lipid membrane 205 be a membrane receptor-related heterotrimeric G protein. It is preferable that the G protein implanted in the artificial lipid membrane 205 be activated by the GPCR.

In Embodiment 2, it is preferable that the ion channel implanted in the artificial lipid membrane 205 be a potassium channel. However, the ion channel implanted in the artificial lipid membrane 205 may be a calcium channel or a sodium channel.

In Embodiment 2, it is preferable that the receptor, the ion channel, or the G protein be implanted in the artificial lipid membrane 205 by the ink-jet method, the minute liquid droplet applying method, the dot impact method, the electrostatic spraying method, the ultrasound method, or electroporation. In the present embodiment, a membrane protein produced on a cell membrane of a cell may be implanted in the artificial lipid membrane 205 by fusing the cell to the artificial lipid membrane 205. The cell may be fused to the artificial lipid membrane 205 by the ink-jet method, the minute liquid droplet applying method, the dot impact method, the electrostatic spraying method, the ultrasound method, or the electroporation. In the present embodiment, a membrane protein arranged on a vesicle membrane of a vesicle may be implanted in the artificial lipid membrane 205 by fusing the vesicle to the artificial lipid membrane 205. In the present embodiment, it is preferable that a series of steps from the first electrolytic solution adding step to the artificial lipid membrane forming step be carried out at a temperature of not lower than 20° C. and not higher than 60° C., and it is more preferable that a series of steps from the first electrolytic solution adding step to the artificial lipid membrane forming step be carried out at a temperature of not lower than 25° C. and not higher than 40° C.

Biosensors can be manufactured by using the artificial lipid membrane forming method of Embodiment 2. The biosensor according to the artificial lipid membrane forming method of the present embodiment is applicable to devices that are the same as the devices to which the biosensor according to the artificial lipid membrane forming method of Embodiment 1 is applicable.

EXAMPLE

Whether or not each of the first electrolytic solution 201 and the second electrolytic solution 204 leaked to the outside of the first chamber 104 and the outside of the second chamber 105 was determined in accordance with the following procedure. The state of the evaporation of each of the first electrolytic solution 201 and the second electrolytic solution 204 was evaluated by using a microscope (VH-6300 produced by Keyence Corporation).

Step A: Preparing Step

An acrylic board was used as each of the first substrate 301 and the second substrate 302 shown in FIG. 9. The thickness of each of the first substrate 301 and the second substrate 302 was adjusted to 0.5 mm, 1 mm, or 5 mm in accordance with the amount of each of the first electrolytic solution 201 and the second electrolytic solution 204. When the amount of each of the first electrolytic solution 201 and the second electrolytic solution 204 was 0.1 µl or 1 µl, the thickness of each of the first substrate 301 and the second substrate 302 was 0.5 mm. When the amount of each of the first electrolytic solution 201 and the second electrolytic solution 204 was 50 µl, the thickness of each of the first substrate 301 and the second substrate 302 was 1 mm. When the amount of each of the first electrolytic solution 201 and the second electrolytic solution 204 was 200 µl, 300 µl, or 400 µl, the thickness of each of the first substrate 301 and the second substrate 302 was 5 mm.

The size of each of the first substrate 301 and the second substrate 302 was 20 mm×20 mm. The container 101 was transparent. The diameter of each of the first chamber 104 and the second chamber 105 was set to 1 mm, 6 mm, or 10 mm in accordance with the amount of each of the first electrolytic solution 201 and the second electrolytic solution 204. When the amount of each of the first electrolytic solution 201 and the second electrolytic solution 204 was 0.1 µl or 1 µl, the diameter of each of the first chamber 104 and the second chamber 105 was 1 mm. When the amount of each of the first electrolytic solution 201 and the second electrolytic solution 204 was 50 µl, the diameter of each of the first chamber 104 and the second chamber 105 was 6 mm. When the amount of each of the first electrolytic solution 201 and the second electrolytic solution 204 was 200 µl, 300 µl, or 400 µl, the diameter of each of the first chamber 104 and the second chamber 105 was 10 mm.

The dividing wall 102 was a Teflon (trademark) film having a thickness of 50 μm and had an insulation property. The surface of the dividing wall 102 was water-repellent. The area of the dividing wall 102 was 4 cm². The container 101 was divided into the first chamber 104 and the second chamber 105 by the dividing wall 102. The artificial lipid membrane forming portion 103 was a circular through hole having a diameter of 200 μm. One artificial lipid membrane forming portion 103 was formed at a center portion of the dividing wall 102 with a drill. The dividing wall 102 was sandwiched between the first substrate 301 and the second substrate 302 to form the artificial lipid membrane forming apparatus 100.

A Compact chamber (Ionovation GmbH) was used only for the artificial lipid membrane forming apparatus 100 in which the amount of each of the first electrolytic solution 201 and the second electrolytic solution 204 was 1 ml. The dividing wall 102 was a Teflon (trademark) film having a thickness of 25 μm and had the insulation property. The surface of the dividing wall 102 was water-repellent. The area of the dividing wall 102 was 1 cm². A surface where the dividing wall 102 and the first electrolytic solution 201 contacted each other was a circle having a diameter of 5 mm. The container 101 was divided into the first chamber 104 and the second chamber 105 by the dividing wall 102. The artificial lipid membrane forming portion 103 was a through hole having a diameter of 120 μm. One artificial lipid membrane forming portion 103 was formed at the center portion of the dividing wall 102 with a laser.

A Tyrode solution was used as each of the first electrolytic solution 201 and the second electrolytic solution 204. The composition of the Tyrode solution was 137 mM of NaCl (Special Grade, produced by Wako Pure Chemical Industries, Ltd.), 2.68 mM of KCl (Special Grade, produced by Wako Pure Chemical Industries, Ltd.), 1.8 mM of $CaCl_2$ (Special Grade, produced by Wako Pure Chemical Industries, Ltd.), 0.32 mM of $NaH_2PO_4$ (Special Grade, produced by Wako Pure Chemical Industries, Ltd.), 5.56 mM of Glucose (SIGMA G-7021), and 1.16 mM of $NaHCO_3$ (Special Grade, produced by Wako Pure Chemical Industries, Ltd.). The viscosity of each of the first electrolytic solution 201 and the second electrolytic solution 204 was adjusted with glycerin (Special Grade, produced by Wako Pure Chemical Industries, Ltd.), polyvinyl alcohol (PVA) (First Grade, produced by Wako Pure Chemical Industries, Ltd., Polymerization Degree: 3,100 to 3,900), or polyethylene glycol (PEG) (First Grade, produced by Wako Pure Chemical Industries, Ltd., Average Molecular Weight: 7,300 to 9,300). The viscosity of each of the first electrolytic solution 201 and the second electrolytic solution 204 was measured with a viscometer (TV-22) produced by Toki Sangyo Co., Ltd.

As the lipid solution 202, a mixture of phosphatide (1,2-diphytanoyl-sn-glycero-3-phosphocholine, produced by Avanti Polar Lipids, Inc.) and organic solvent (chloroform, produced by Wako Pure Chemical Industries, Ltd.) was used. The concentration of the phosphatide was 1 mg/ml.

Step B: First Electrolytic Solution Adding Step

The first electrolytic solution 201 was added to the first chamber 104 with a pipette (produced by Gilson, Inc.). Used as the first electrolytic solution 201 was the Tyrode solution with viscosity adjusted with use of glycerin, PVA, or PEG. The temperature of the first electrolytic solution 201 was 22° C.

Step C: Lipid Solution Adding Step

1 μl of the lipid solution 202 was added from the second chamber 105 side to the artificial lipid membrane forming portion 103. A microsyringe (produced by Hamilton Company) was used for this addition. When the lipid solution 202 was added to the artificial lipid membrane forming portion 103, the lipid solution 202 reached the artificial lipid membrane forming portion 103 while spreading on the surface of the dividing wall 102.

Step D: Second Electrolytic Solution Adding Step

The second electrolytic solution 204 was added to the second chamber 105 with a pipette (produced by Gilson, Inc.). Used as the second electrolytic solution 204 was the Tyrode solution with viscosity adjusted with use of glycerin, PVA, or PEG. The temperature of the second electrolytic solution 204 was 22° C.

Step E: Artificial Lipid Membrane Forming Step

The artificial lipid membrane forming apparatus 100 was placed.

Whether or not each of the first electrolytic solution 201 and the second electrolytic solution 204 leaked when the artificial lipid membrane forming apparatus 100 was placed at an angle of 45°, 90°, or 180° with respect to a horizontal surface was determined after the artificial lipid membrane forming step. Placing the artificial lipid membrane forming apparatus 100 at an angle of 90° with respect to the horizontal surface denotes that the opening of the second chamber 105 faces in the horizontal direction. Placing the artificial lipid membrane forming apparatus 100 at an angle of 180° with respect to the horizontal surface denotes that the opening of the second chamber 105 faces in a vertically downward direction. Whether or not each of the first electrolytic solution 201 and the second electrolytic solution 204 leaked when the artificial lipid membrane forming apparatus 100 was inclined or turned over was confirmed by this determination.

In the steps from the first electrolytic solution adding step until the artificial lipid membrane forming step, the room temperature was 22° C., and the relative humidity was 50%.

Table 1 shows the viscosity of each of the first electrolytic solution 201 and the second electrolytic solution 204, the viscosity being adjusted with glycerin.

TABLE 1

| Glycerin Concentration (%) | Viscosity (mPa · s) |
|---|---|
| 0.5 | 1.28 |
| 1 | 1.31 |
| 5 | 1.53 |
| 25 | 2.71 |
| 50 | 8.75 |
| 75 | 200 |
| 99 | 1,500 |

Table 2 shows the viscosity of each of the first electrolytic solution 201 and the second electrolytic solution 204, the viscosity being adjusted with PVA.

TABLE 2

| PVA Concentration (w/w %) | Viscosity (mPa · s) |
|---|---|
| 0.087 | 1.4 |
| 0.87 | 2.8 |
| 1.75 | 5 |
| 12 | 200 |
| 20 | 2,000 |

Figure 17:
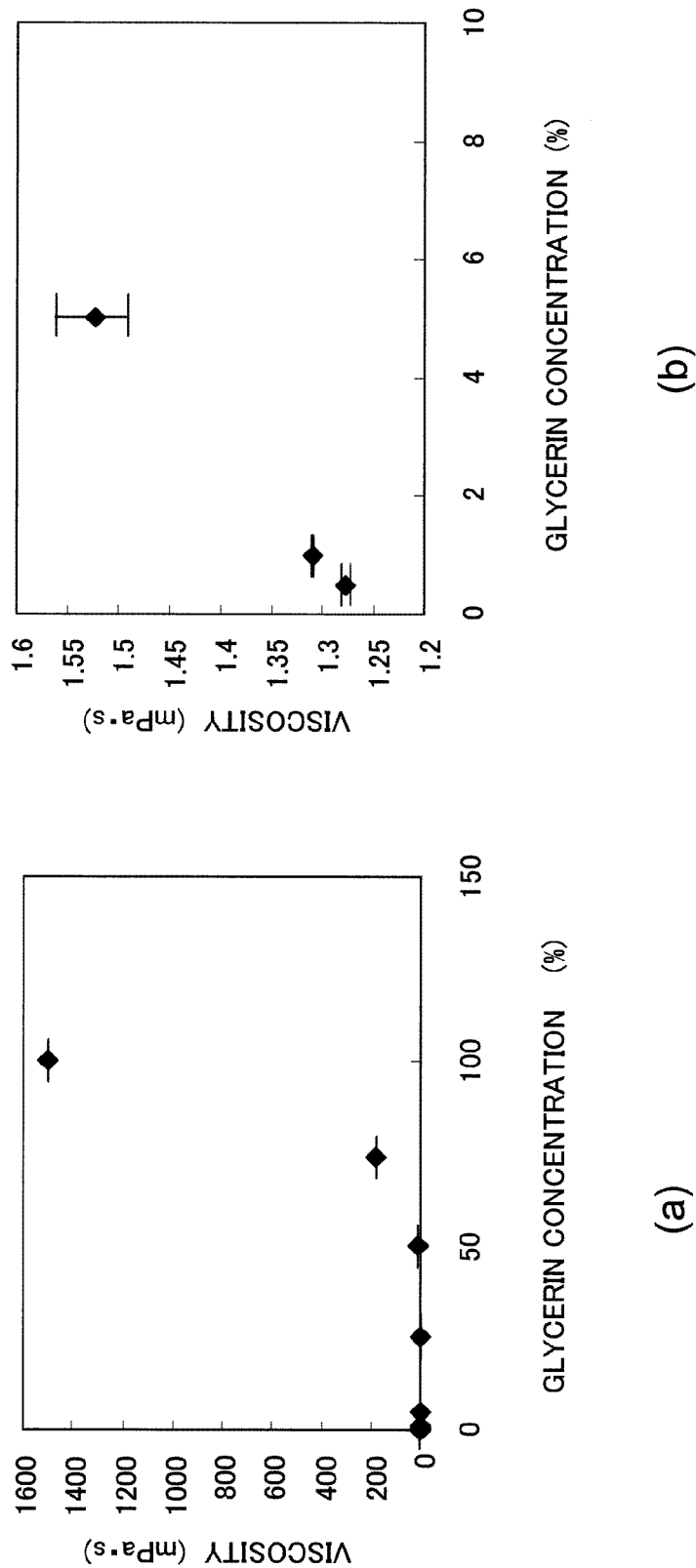
FIG. 17 shows a relation between a glycerin concentration and a viscosity of an electrolytic solution.
Figure 18:
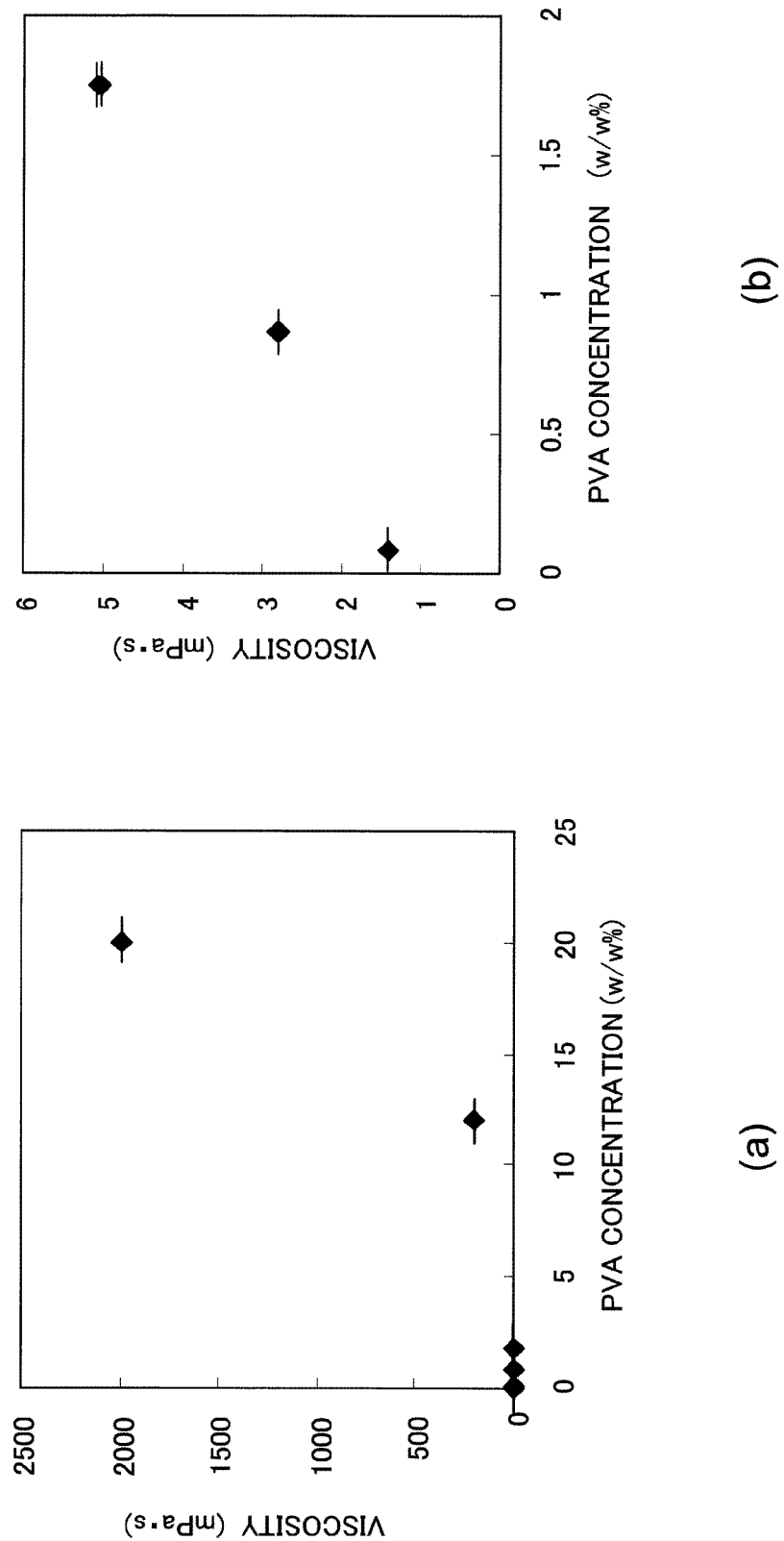
FIG. 18 shows a relation between a PVA concentration and the viscosity of the electrolytic solution.

FIGS. 17(a) and 17(b) show the viscosity of each of the first electrolytic solution 201 and the second electrolytic solution 204, the viscosity being adjusted with glycerin. FIG. 17(b) shows an enlarged view of a low-concentration region of FIG. 17(a). FIGS. 18 show the viscosity of each of the first electrolytic solution 201 and the second electrolytic solution 204, the viscosity being adjusted with PVA. FIG. 18(b) shows an enlarged view of a low-concentration region of FIG. 18(a). The viscosity of each of the first electrolytic solution 201 and the second electrolytic solution 204 increased as the concentration of glycerin or PVA increased. When adjusting the viscosity of each of the first electrolytic solution 201 and the second electrolytic solution 204 with glycerin or PVA, the ion concentration of each of the first electrolytic solution 201 and the second electrolytic solution 204 was maintained constant. When adjusting the viscosity of each of the first electrolytic solution 201 and the second electrolytic solution 204, the viscosity of each of the first electrolytic solution 201 and the second electrolytic solution 204 increased together with the increase in the concentration of PEG. When adjusting the viscosity of each of the first electrolytic solution 201 and the second electrolytic solution 204 with PEG, the ion concentration of each of the first electrolytic solution 201 and the second electrolytic solution 204 was maintained constant.

Tables 3 and 4 shows result of the determination regarding the leakage of each of the first electrolytic solution 201 and the second electrolytic solution 204 each of with viscosity adjusted with glycerin.

TABLE 3

| Amount | Viscosity (mPa·s) | Angles | | |
|---|---|---|---|---|
| | | 45° | 90° | 180° |
| 1 ml | 1.24 | − | − | − |
| | 1.28 | − | − | − |
| | 1.31 | − | − | − |
| | 2.71 | − | − | − |
| | 8.75 | − | − | − |
| | 200 | − | − | − |
| | 1500 | − | − | − |
| 400 μl | 1.24 | − | − | − |
| | 1.28 | + | − | − |
| | 1.31 | + | − | − |
| | 2.71 | + | − | − |
| | 8.75 | + | − | − |
| | 200 | + | − | − |
| | 1500 | + | + | + |
| 300 μl | 1.24 | − | − | − |
| | 1.28 | + | − | − |
| | 1.31 | + | − | − |
| | 2.71 | + | − | − |
| | 8.75 | + | − | − |
| | 200 | + | − | − |
| | 1500 | + | + | + |
| 200 μl | 1.24 | + | + | + |
| | 1.28 | + | + | + |
| | 1.31 | + | + | + |
| | 2.71 | + | + | + |
| | 8.75 | + | + | + |
| | 200 | + | + | + |
| | 1500 | + | + | + |
| 50 μl | 1.24 | + | + | + |
| | 1.28 | + | + | + |
| | 1.31 | + | + | + |
| | 2.71 | + | + | + |
| | 8.75 | + | + | + |
| | 200 | + | + | + |
| | 1500 | + | + | + |

TABLE 4

| Amount | Viscosity (mPa·s) | Angles | | |
|---|---|---|---|---|
| | | 45° | 90° | 180° |
| 1 μl | 1.24 | + | + | + |
| | 1.28 | + | + | + |
| | 1.31 | + | + | + |

TABLE 4-continued

| Amount | Viscosity (mPa·s) | Angles | | |
|---|---|---|---|---|
| | | 45° | 90° | 180° |
| | 2.71 | + | + | + |
| | 8.75 | + | + | + |
| | 200 | + | + | + |
| | 1500 | + | + | + |
| 0.1 μl | 1.24 | + | + | + |
| | 1.28 | + | + | + |
| | 1.31 | + | + | + |
| | 2.71 | + | + | + |
| | 8.75 | + | + | + |
| | 200 | + | + | + |
| | 1500 | + | + | + |
| 10 pl | 1.24 | + | + | + |
| | 2.71 | + | + | + |
| | 2.85 | + | + | + |

Table 5 shows results of the determination regarding the leakage of each of the first electrolytic solution 201 and the second electrolytic solution 204. The viscosity of each of those solutions was adjusted with PVA.

TABLE 5

| Amount | Viscosity (mPa·s) | Angles | | |
|---|---|---|---|---|
| | | 45° | 90° | 180° |
| 1 ml | 1.24 | − | − | − |
| | 1.4 | − | − | − |
| | 2.8 | − | − | − |
| | 5 | − | − | − |
| | 200 | − | − | − |
| | 2000 | − | − | − |
| 400 μl | 1.24 | − | − | − |
| | 1.4 | − | − | − |
| | 2.8 | − | − | − |
| | 5 | − | − | − |
| | 200 | − | − | − |
| | 2000 | − | − | − |
| 300 μl | 1.24 | − | − | − |
| | 1.4 | − | − | − |
| | 2.8 | − | − | − |
| | 5 | + | − | − |
| | 200 | + | − | − |
| | 2000 | + | + | + |
| 200 μl | 1.24 | + | + | + |
| | 1.4 | + | + | + |
| | 2.8 | + | + | + |
| | 5 | + | + | + |
| | 200 | + | + | + |
| | 2000 | + | + | + |
| 50 μl | 1.24 | + | + | + |
| | 1.4 | + | + | + |
| | 2.8 | + | + | + |
| | 5 | + | + | + |
| | 200 | + | + | + |
| | 2000 | + | + | + |
| 1 μl | 1.24 | + | + | + |
| | 1.4 | + | + | + |
| | 2.8 | + | + | + |
| | 5 | + | + | + |
| | 200 | + | + | + |
| | 2000 | + | + | + |
| 0.1 μl | 1.24 | + | + | + |
| | 1.4 | + | + | + |
| | 2.8 | + | + | + |
| | 5 | + | + | + |
| | 200 | + | + | + |
| | 2000 | + | + | + |

In the above tables, "+" denotes that each of the first electrolytic solution 201 and the second electrolytic solution 204 did not leak through the opening of the inlet or outlet to the outside of the first chamber 104 and the outside of the second chamber 105. In addition, in the above tables, "–" denotes that each of the first electrolytic solution 201 and the second electrolytic solution 204 leaked through the opening of the inlet or outlet to the outside of the first chamber 104 and the outside of the second chamber 105.

As shown in Tables 3 and 4, when the viscosity was adjusted with glycerin, and the amount of each of the first electrolytic solution 201 and the second electrolytic solution 204 was 200 μl or smaller, each of the first electrolytic solution 201 and the second electrolytic solution 204 did not leak to the outside of the first chamber 104 and the outside of the second chamber 105. When the amount of each of the first electrolytic solution 201 and the second electrolytic solution 204 was 300 μl or greater, each of the first electrolytic solution 201 and the second electrolytic solution 204 leaked to the outside of the first chamber 104 and the outside of the second chamber 105 in some cases.

As shown in Table 4, when the viscosity was adjusted with glycerin, and the amount of each of the first electrolytic solution 201 and the second electrolytic solution 204 was 10 pl, each of the first electrolytic solution 201 and the second electrolytic solution 204 did not leak to the outside of the chamber.

Figure 19:
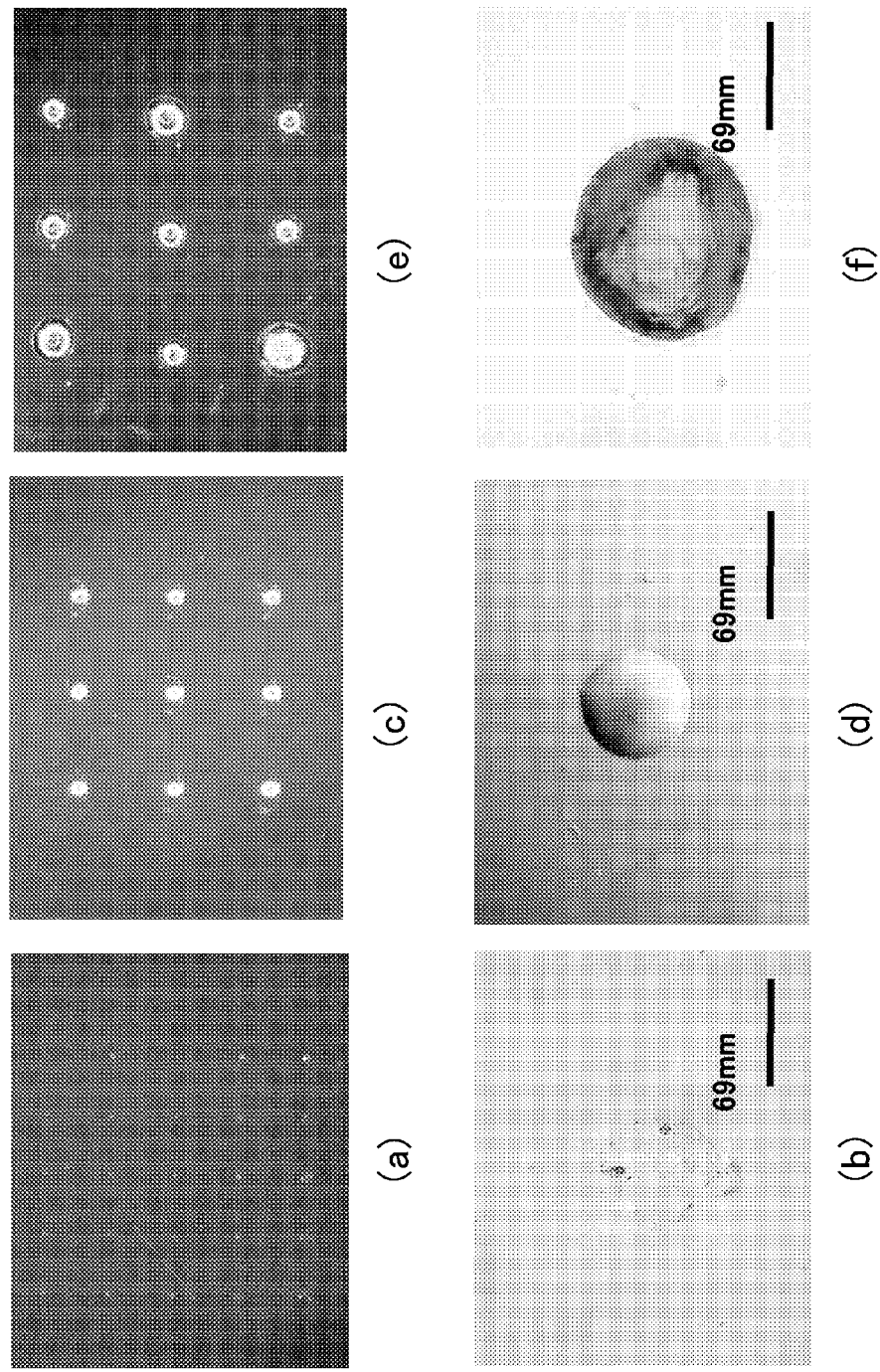
FIG. 19 shows a micrograph of the electrolytic solution in a first chamber in Embodiment 2.
Figure 20:
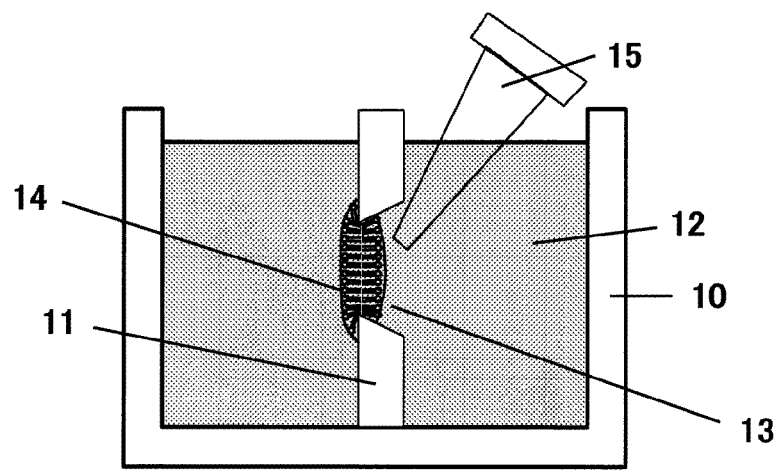
FIG. 20 shows a conventional artificial lipid membrane forming method (bubble spraying method).
Figure 21:
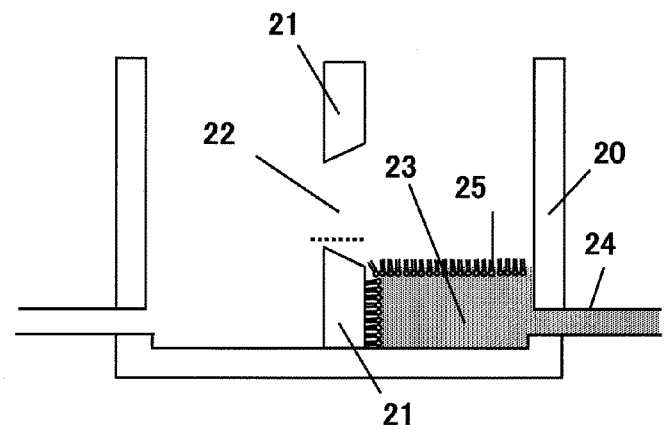
FIG. 21 shows a conventional artificial lipid membrane forming method (attaching method).
Figure 21:
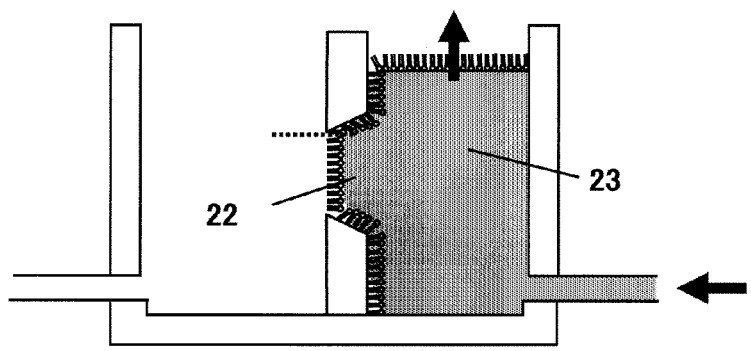
Figure 21:
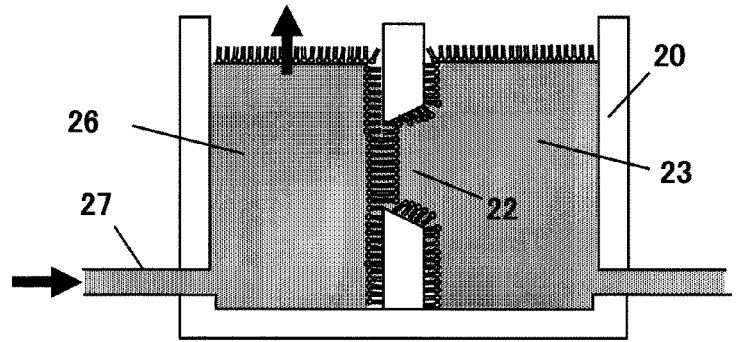
Figure 22:
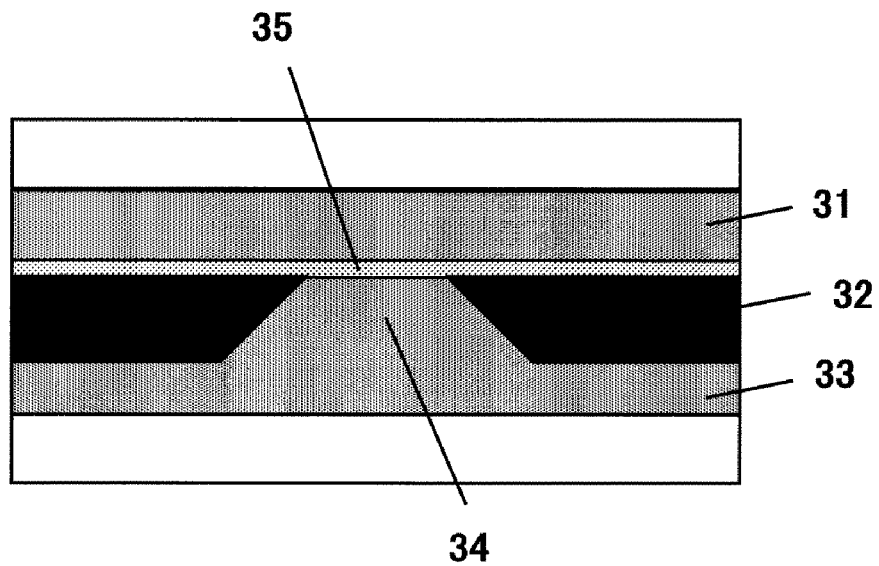
FIG. 22 shows the artificial lipid membrane forming apparatus of PTL 1.

FIG. 19 shows a micrograph of a liquid droplet in the first chamber 104 immediately after 10 pl of the first electrolytic solution 201 is added by the minute liquid droplet applying method. In the present example, the first electrolytic solution 201 or the second electrolytic solution 204 was filled in a glass tube having an inner diameter of 300 μm, and the first electrolytic solution 201 or the second electrolytic solution 204 was applied to the first chamber 104 or the second chamber 105 by the piston movement of a stainless steel needle having an outer diameter of 300 μm. FIG. 19(a) shows the liquid droplet in a case where the viscosity of the first electrolytic solution 201 is 1.24 mPa·s. FIG. 19(b) shows an enlarged view of FIG. 19(a). FIG. 19(c) shows the liquid droplet in a case where the viscosity of the first electrolytic solution 201 is 2.71 mPa·s. The viscosity of the first electrolytic solution 201 was adjusted with glycerin. FIG. 19(d) shows an enlarged view of FIG. 19(c). FIG. 19(e) shows the liquid droplet in a case where the viscosity of the first electrolytic solution 201 is 2.85 mPa·s. FIG. 19(f) shows an enlarged view of FIG. 19(e).

When the viscosity of the first electrolytic solution 201 was 2.71 mPa·s or 2.85 mPa·s, the first electrolytic solution 201 did not leak to the outside of the first chamber 104. When the viscosity of the second electrolytic solution 204 was 2.71 mPa·s or 2.85 mPa·s, the second electrolytic solution 204 did not leak to the outside of the second chamber 105.

When the amount of each of the first electrolytic solution 201 and the second electrolytic solution 204 was 10 pl or smaller, the amount of each of the first electrolytic solution 201 and the second electrolytic solution 204 was too small, so that each of the first electrolytic solution 201 and the second electrolytic solution 204 could not be added by the minute liquid droplet applying method.

As shown in Table 5, in a case where the viscosity was adjusted with PVA, and the amount of each of the first electrolytic solution 201 and the second electrolytic solution 204 was 200 μl or smaller, each of the first electrolytic solution 201 and the second electrolytic solution 204 did not leak to the outside of the chamber. When the amount of each of the first electrolytic solution 201 and the second electrolytic solution 204 was 300 μl or greater, each of the first electrolytic solution 201 and the second electrolytic solution 204 leaked to the outside of the chamber.

When the viscosity was adjusted with PEG, and the amount of each of the first electrolytic solution 201 and the second electrolytic solution 204 was 200 μl or smaller, each of the first electrolytic solution 201 and the second electrolytic solution 204 did not leak to the outside of the chamber. When the amount of each of the first electrolytic solution 201 and the second electrolytic solution 204 was 300 μl or greater, each of the first electrolytic solution 201 and the second electrolytic solution 204 leaked to the outside of the chamber.

In a case where the glycerin concentration of the first electrolytic solution 201 was 99%, that is, in a case where the viscosity of the first electrolytic solution 201 was 1,500 mPa·s, the reagent of the Tyrode solution could not dissolve in the first electrolytic solution 201. In this case, since the first electrolytic solution 201 was adhered to an inner wall of the first chamber 104, the artificial lipid membrane 205 could not be formed.

When the glycerin concentration of the second electrolytic solution 204 was 99%, that is, the viscosity of the second electrolytic solution 204 was 1,500 mPa·s, the reagent of the Tyrode solution could not dissolve in the second electrolytic solution 204. In this case, since the second electrolytic solution 204 was adhered to an inner wall of the second chamber 105, the artificial lipid membrane 205 could not be formed.

When the PVA concentration of the first electrolytic solution 201 was 20 w/w %, that is, the viscosity of the first electrolytic solution 201 was 2,000 mPa·s, the first electrolytic solution 201 was adhered to the inner wall of the first chamber 104, so that the artificial lipid membrane 205 could not be formed. When the PVA concentration of the second electrolytic solution 204 was 20 w/w %, that is, in a case where the viscosity of the second electrolytic solution 204 was 2,000 mPa·s, the second electrolytic solution 204 was adhered to the inner wall of the second chamber 105, so that the artificial lipid membrane 205 could not be formed.

In accordance with the foregoing, when the amount of each of the first electrolytic solution 201 and the second electrolytic solution 204 was not smaller than 10 pl and not larger than 200 μl, and the viscosity of each of the first electrolytic solution 201 and the second electrolytic solution 204 was not lower than 1.3 mPa·s and not higher than 200 mPa·s, each of the first electrolytic solution 201 and the second electrolytic solution 204 did not leak to the outside of the first chamber 104 and the outside of the second chamber 105 even though the artificial lipid membrane forming apparatus 100 was inclined or turned over.

The state of the evaporation of each of the first electrolytic solution 201 and the second electrolytic solution 204 was observed with a microscope (VH-6300 produced by Keyence Corporation). As a result, as compared to a case where the viscosity of each of the first electrolytic solution 201 and the second electrolytic solution 204 was lower than 1.3 mPa·s, it was confirmed that in a case where the viscosity of each of the first electrolytic solution 201 and the second electrolytic solution 204 was not lower than 1.3 mPa·s and not higher than 200 mPa·s, the evaporation of each of the first electrolytic solution 201 and the second electrolytic solution 204 was suppressed.

Comparative Example 1

The Tyrode solution was used as each of the first electrolytic solution 201 and the second electrolytic solution 204. Whether or not each of the first electrolytic solution 201 and the second electrolytic solution 204 leaked to the outside of the chamber was determined in accordance with the following procedure.

Preparing Step

An acrylic board was used as each of the first substrate 301 and the second substrate 302 shown in FIG. 9. The thickness of each of the first substrate 301 and the second substrate 302 was adjusted to 0.5 mm, 1 mm, or 5 mm in accordance with the amount of each of the first electrolytic solution 201 and the second electrolytic solution 204. When the amount of each of the first electrolytic solution 201 and the second electrolytic solution 204 was 0.1 μl or 1 μl, the thickness of each of the first substrate 301 and the second substrate 302 was 0.5 mm. When the amount of each of the first electrolytic solution 201 and the second electrolytic solution 204 was 50 μl, the thickness of each of the first substrate 301 and the second substrate 302 was 1 mm. When the amount of each of the first electrolytic solution 201 and the second electrolytic solution 204 was 200 μl, 300 μl, or 400 μl, the thickness of each of the first substrate 301 and the second substrate 302 was 5 mm.

The size of each of the first substrate 301 and the second substrate 302 was 20 mm×20 mm. The container 101 was transparent. The diameter of each of the first chamber 104 and the second chamber 105 was set to 1 mm, 6 mm, or 10 mm in accordance with the amount of each of the first electrolytic solution 201 and the second electrolytic solution 204. When the amount of each of the first electrolytic solution 201 and the second electrolytic solution 204 was 0.1 μl or 1 μl, the diameter of each of the first chamber 104 and the second chamber 105 was 1 mm. When the amount of each of the first electrolytic solution 201 and the second electrolytic solution 204 was 50 μl, the diameter of each of the first chamber 104 and the second chamber 105 was 6 mm. When the amount of each of the first electrolytic solution 201 and the second electrolytic solution 204 was 200 μl, 300 μl, or 400 μl, the diameter of each of the first chamber 104 and the second chamber 105 was 10 mm.

The dividing wall 102 was a Teflon (trademark) film having a thickness of 50 μm and had the insulation property. The surface of the dividing wall 102 was water-repellent. The area of the dividing wall 102 was 4 cm². The container 101 was divided into the first chamber 104 and the second chamber 105 by the dividing wall 102. The artificial lipid membrane forming portion 103 was a circular through hole having a diameter of 200 μm. The artificial lipid membrane forming apparatus 100 in which one artificial lipid membrane forming portion 103 was formed at a center portion of the dividing wall 102 with a drill. The dividing wall 102 was sandwiched between the first substrate 301 and the second substrate 302 to form the artificial lipid membrane forming apparatus 100.

The above-described Compact chamber (Ionovation GmbH) was used only for the artificial lipid membrane forming apparatus 100 in which the amount of each of the first electrolytic solution 201 and the second electrolytic solution 204 was 1 ml. The dividing wall 102 was a Teflon (trademark) film having a thickness of 25 μm and had the insulation property. The surface of the dividing wall 102 was water-repellent. The area of the dividing wall 102 was 1 cm². A surface where the dividing wall 102 and the first electrolytic solution 201 contacted each other was a circle having a diameter of 5 mm. The container 101 was divided into the first chamber 104 and the second chamber 105 by the dividing wall 102. The artificial lipid membrane forming portion 103 was a through hole having a diameter of 120 μm. One artificial lipid membrane forming portion 103 was formed at the center portion of the dividing wall 102 with a laser.

The composition of the Tyrode solution was 137 mM of NaCl (Special Grade, produced by Wako Pure Chemical Industries, Ltd.), 2.68 mM of KCl (Special Grade, produced by Wako Pure Chemical Industries, Ltd.), 1.8 mM of $CaCl_2$ (Special Grade, produced by Wako Pure Chemical Industries, Ltd.), 0.32 mM of $NaH_2PO_4$ (Special Grade, produced by Wako Pure Chemical Industries, Ltd.), 5.56 mM of Glucose (SIGMA G-7021), and 1.16 mM of $NaHCO_3$ (Special Grade, produced by Wako Pure Chemical Industries, Ltd.). The viscosity of each of the first electrolytic solution 201 and the second electrolytic solution 204 was measured with using a viscometer (TV-22 produced by Toki Sangyo Co., Ltd.). The viscosity of each of the first electrolytic solution 201 and the second electrolytic solution 204 was 1.24 mPa·s.

As the lipid solution 202, a mixture of phosphatide (1,2-diphytanoyl-sn-glycero-3-phosphocholine, produced by Avanti Polar Lipids, Inc.) and organic solvent (chloroform, produced by Wako Pure Chemical Industries, Ltd.) was used. The concentration of the phosphatide was 1 mg/ml.

First Electrolytic Solution Adding Step

The first electrolytic solution 201 was added to the first chamber 104 by a pipette (produced by Gilson, Inc.). The temperature of the first electrolytic solution 201 was 22° C.

Lipid Solution Adding Step

1 μl of the lipid solution 202 was added from the second chamber 105 side to the artificial lipid membrane forming portion 103. A microsyringe (produced by Hamilton Company) was used for this addition. When the lipid solution 202 was added to the artificial lipid membrane forming portion 103, the lipid solution 202 reached the artificial lipid membrane forming portion 103 while spreading on the surface of the dividing wall 102.

Second Electrolytic Solution Adding Step

The second electrolytic solution 204 was added to the second chamber 105 with a pipette (produced by Gilson, Inc.). The temperature of the second electrolytic solution 204 was 22° C.

Artificial Lipid Membrane Forming Step

The artificial lipid membrane forming apparatus 100 was placed.

Whether or not each of the first electrolytic solution 201 and the second electrolytic solution 204 leaked when the artificial lipid membrane forming apparatus 100 was placed at an angle of 45°, 90°, or 180° with respect to a horizontal surface was determined after the artificial lipid membrane forming step. Whether or not each of the first electrolytic solution 201 and the second electrolytic solution 204 leaked when the artificial lipid membrane forming apparatus 100 was inclined or turned over was confirmed by this determination.

In the steps from the first electrolytic solution adding step until the artificial lipid membrane forming step, the room temperature was 22° C., and the relative humidity was 50%.

When the amount of the first electrolytic solution 201 was 300 μl or greater, the first electrolytic solution 201 leaked to the outside of the first chamber 104. When the amount of the second electrolytic solution 204 was 300 μl or greater, the second electrolytic solution 204 leaked to the outside of the second chamber 105.

The viscosity of each of the first electrolytic solution 201 and the second electrolytic solution 204 was 1.24 mPa·s, and the amount of each of the first electrolytic solution 201 and the second electrolytic solution 204 was 10 pl. Since the first electrolytic solution 201 rapidly evaporated, the first electrolytic solution 201 could not be added to the first chamber 104. Similarly, since the second electrolytic solution 204 rapidly evaporated, the second electrolytic solution 204 could not be added to the second chamber 105.

The first electrolytic solution 201 having the viscosity of 1.24 mPa·s had a higher evaporation rate than the first electrolytic solution 201 having the viscosity of not lower than 1.3 mPa·s and not higher than 200 mPa·s, so that when the amount of the first electrolytic solution 201 was not smaller than 10 pl and not larger than 200 µl, it was difficult to form the artificial lipid membrane 205. The second electrolytic solution 204 having the viscosity of 1.24 mPa·s had a higher evaporation rate than the second electrolytic solution 204 having the viscosity of not lower than 1.3 mPa·s and not higher than 200 mPa·s, so that in a case where the amount of the second electrolytic solution 204 was not smaller than 10 pl and not larger than 200 µl, the formation of the artificial lipid membrane 205 was difficult.

Comparative Example 2

As each of the first electrolytic solution 201 and the second electrolytic solution 204, a 0.1 KCl aqueous solution containing 0.1 M of Glucose was used. As with Comparative Example 1, whether or not each of the first electrolytic solution 201 and the second electrolytic solution 204 leaked to the outside of the first chamber 104 and the outside of the second chamber 105 were determined.

Used as each of the first electrolytic solution 201 and the second electrolytic solution 204 was an aqueous solution containing 0.1 M of Glucose (SIGMA G-7021) and 0.1 M of KCl (Special Grade, produced by Wako Pure Chemical Industries, Ltd.). The viscosity of each of the first electrolytic solution 201 and the second electrolytic solution 204 was measured with a viscometer (TV-22) produced by Toki Sangyo Co., Ltd. The viscosity of each of the first electrolytic solution 201 and the second electrolytic solution 204 was 1.24 mPa·s.

The lipid solution 202 was the same as in Comparative Example 1.

First Electrolytic Solution Adding Step

The first electrolytic solution 201 was added to the first chamber 104 with a pipette (produced by Gilson, Inc.). The temperature of the first electrolytic solution 201 was 22° C.

Lipid Solution Adding Step

1 µl of the lipid solution 202 was added from the second chamber 105 side to the artificial lipid membrane forming portion 103. A microsyringe (produced by Hamilton Company) was used for this addition. When the lipid solution 202 was added to the artificial lipid membrane forming portion 103, the lipid solution 202 reached the artificial lipid membrane forming portion 103 while spreading on the surface of the dividing wall 102.

Second Electrolytic Solution Adding Step

The second electrolytic solution 204 was added to the second chamber 105 by a pipette (produced by Gilson, Inc.). The temperature of the second electrolytic solution 204 was 22° C.

Artificial Lipid Membrane Forming Step

The artificial lipid membrane forming apparatus 100 was placed.

Whether or not each of the first electrolytic solution 201 and the second electrolytic solution 204 leaked when the artificial lipid membrane forming apparatus 100 was placed at an angle of 45°, 90°, or 180° with respect to a horizontal surface was determined after the artificial lipid membrane forming step. Whether or not each of the first electrolytic solution 201 and the second electrolytic solution 204 leaked when the artificial lipid membrane forming apparatus 100 was inclined or turned over was confirmed by this determination.

In the steps from the first electrolytic solution adding step until the artificial lipid membrane forming step, the room temperature was 22° C., and the relative humidity was 50%.

Table 6 shows results of the determination regarding the leakage of each of the first electrolytic solution 201 and the second electrolytic solution 204 when the 0.1M KCl aqueous solution containing 0.1 M of Glucose was used as each of the first electrolytic solution 201 and the second electrolytic solution 204.

TABLE 6

| Amount | Viscosity (mPa · s) | Angles | | |
|---|---|---|---|---|
| | | 45° | 90° | 180° |
| 1 ml | 1.24 | − | − | − |
| 400 µl | 1.24 | − | − | − |
| 300 µl | 1.24 | − | − | − |
| 200 µl | 1.24 | − | − | − |
| 50 µl | 1.24 | + | + | + |
| 1 µl | 1.24 | + | + | + |
| 0.1 µl | 1.24 | + | + | + |

When the amount of the first electrolytic solution 201 was not smaller than 200 µl, the first electrolytic solution 201 leaked to the outside of the first chamber 104. When the amount of the second electrolytic solution 204 was not smaller than 200 µl, the second electrolytic solution 204 leaked to the outside of the second chamber 105.

When the amount of the first electrolytic solution 201 was 10 pl, the first electrolytic solution 201 rapidly evaporated, so that the first electrolytic solution 201 could not be added to the first chamber 104. When the amount of the second electrolytic solution 204 was 10 pl, the second electrolytic solution 204 rapidly evaporated, so that the second electrolytic solution 204 could not be added to the second chamber 105.

The first electrolytic solution 201 having the viscosity of 1.24 mPa·s had a higher evaporation rate than the first electrolytic solution 201 having the viscosity of not lower than 1.3 mPa·s and not higher than 200 mPa·s, so that when the amount of the first electrolytic solution 201 was not smaller than 10 pl and not larger than 200 µl, it was difficult to form the artificial lipid membrane. The second electrolytic solution 204 having the viscosity of 1.24 mPa·s had a higher evaporation rate than the second electrolytic solution 204 having the viscosity of not lower than 1.3 mPa·s and not higher than 200 mPa·s, so that when the amount of the second electrolytic solution 204 was not smaller than 10 pl and not larger than 200 µl, it was difficult to form the artificial lipid membrane.

From the foregoing explanation, many modifications and other embodiments of the present invention are obvious to one skilled in the art. Therefore, the foregoing explanation should be interpreted only as an example and is provided for the purpose of teaching the best mode for carrying out the present invention to one skilled in the art. The structures and/or functional details may be substantially modified within the spirit of the present invention.

INDUSTRIAL APPLICABILITY

The artificial lipid membrane forming method of the present invention is useful in the fields of environment, chemical industry, semiconductor, finance, food, housing, car, security, life, agriculture, forest industry, fishery, transportation, safety, care, welfare, medical treatment, pharmaceutical, and health care.

REFERENCE SIGNS LIST

- 10 container
- 11 flat plate
- 12 electrolytic solution
- 13 minute hole
- 14 lipid solution
- 15 pipette
- 20 container
- 21 flat plate
- 22 minute hole
- 23 electrolytic solution
- 24 inlet
- 25 lipid molecule
- 26 electrolytic solution
- 27 inlet
- 31 first chamber
- 32 dividing wall
- 33 second chamber
- 34 small hole
- 35 artificial lipid membrane
- 100 artificial lipid membrane forming apparatus
- 101 container
- 102 dividing wall
- 103 artificial lipid membrane forming portion
- 104 first chamber
- 105 second chamber
- 106 first opening
- 107 second opening
- 108 electrode
- 201 first electrolytic solution
- 202 lipid solution
- 203 lipid
- 204 second electrolytic solution
- 205 artificial lipid membrane
- 301 first substrate
- 302 second substrate
- 303 first inlet
- 304 outlet
- 305 receptor channel
- 306 ligand
- 307 ion
- 308 channel
- 309 receptor protein
- 310 G protein
- 311 enzyme

The invention claimed is:

1. A method for forming an artificial lipid membrane, comprising the steps of:
   (A) preparing an artificial lipid membrane forming apparatus comprising a first chamber, a second chamber, a dividing wall sandwiched between the first chamber and the second chamber, and an artificial lipid membrane forming portion consisting of a through hole formed on the dividing wall, the first chamber having a capacity of not smaller than 10 pl and not larger than 200 μl, the second chamber having a capacity of not smaller than 10 pl and not larger than 200 μl;
   (B) adding to the first chamber a first electrolytic solution having a viscosity of not lower than 1.3 mPa·s and not higher than 200 mPa·s;
   (C) adding to the artificial lipid membrane forming portion a lipid solution containing a lipid and an organic solvent;
   (D) adding to the second chamber a second electrolytic solution having a viscosity of not lower than 1.3 mPa·s and not higher than 200 mPa·s to sandwich the lipid solution between the first electrolytic solution and the second electrolytic solution; and
   (E) removing the organic solvent to form an artificial lipid membrane at the artificial lipid membrane forming portion.

2. The method according to claim 1, wherein at least one of the first electrolytic solution and the second electrolytic solution contains an organic compound having a hydroxyl group.

3. The method according to claim 2, wherein the organic compound having the hydroxyl group is an alcohol.

4. The method according to claim 3, wherein the alcohol is a lower alcohol.

5. The method according to claim 3, wherein the alcohol is glycerin.

6. The method according to claim 1, wherein at least one of the first electrolytic solution and the second electrolytic solution contains a polymer.

7. The method according to claim 6, wherein at least one of the first electrolytic solution and the second electrolytic solution contains a polyvinyl alcohol.

8. The method according to claim 1, wherein in Step (B), the first electrolytic solution is added to the first chamber by an ink-jet method.

9. The method according to claim 1, wherein in Step (D), the second electrolytic solution is added to the second chamber by an ink-jet method.

10. The method according to claim 1, wherein in Step (C), the lipid solution is added to the artificial lipid membrane forming portion by an ink-jet method.

11. The method according to claim 1, further comprising the step of:
    (F), implanting at least one of a receptor and an ion channel in the artificial lipid membrane after Step (E).

12. The method according to claim 1, wherein in Step (B), the first chamber is filled with the first electrolytic solution.

13. The method according to claim 12, wherein in Step (D), the second chamber is filled with the second electrolytic solution.

14. The method according to claim 1, wherein in Step (D), the second chamber is filled with the second electrolytic solution.

* * * * *